(12) United States Patent
Silver et al.

(10) Patent No.: US 12,138,300 B2
(45) Date of Patent: Nov. 12, 2024

(54) METHODS AND COMPOSITIONS FOR INDUCING NEURAL PLASTICITY

(71) Applicant: CASE WESTERN RESERVE UNIVERSITY, Cleveland, OH (US)

(72) Inventors: Jerry Silver, Bay Village, OH (US); Yu Luo, Shaker Heights, OH (US); Fucheng Luo, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 724 days.

(21) Appl. No.: 17/272,393

(22) PCT Filed: Aug. 29, 2019

(86) PCT No.: PCT/US2019/048698
§ 371 (c)(1),
(2) Date: Mar. 1, 2021

(87) PCT Pub. No.: WO2020/051051
PCT Pub. Date: Mar. 12, 2020

(65) Prior Publication Data
US 2021/0330757 A1    Oct. 28, 2021

Related U.S. Application Data

(60) Provisional application No. 62/727,420, filed on Sep. 5, 2018.

(51) Int. Cl.
| | | |
|---|---|---|
| *A61K 38/46* | (2006.01) | |
| *A61K 9/00* | (2006.01) | |
| *A61P 9/10* | (2006.01) | |
| *A61P 25/28* | (2006.01) | |

(52) U.S. Cl.
CPC .......... *A61K 38/465* (2013.01); *A61K 9/0019* (2013.01); *A61P 9/10* (2018.01); *A61P 25/28* (2018.01); *C12Y 301/03048* (2013.01)

(58) Field of Classification Search
None
See application file for complete search history.

(56) References Cited

U.S. PATENT DOCUMENTS

| | | | |
|---|---|---|---|
| 5,804,604 | A | 9/1998 | Frankel et al. |
| 6,841,535 | B2 | 1/2005 | Divita et al. |
| 9,937,242 | B2 | 4/2018 | Lang et al. |
| 2004/0138255 | A1 | 7/2004 | Huang et al. |
| 2009/0042872 | A1 | 2/2009 | Ryu et al. |
| 2009/0202544 | A1 | 8/2009 | Suciu-Foca et al. |
| 2012/0045459 | A1 | 2/2012 | MacKeigan et al. |
| 2012/0231014 | A1 | 8/2012 | Flanagan et al. |
| 2014/0045762 | A1 | 2/2014 | Flanagan et al. |
| 2015/0084328 | A1 | 3/2015 | Kampfe et al. |
| 2015/0366949 | A1 | 12/2015 | Lang et al. |

FOREIGN PATENT DOCUMENTS

| | | |
|---|---|---|
| EP | 0028742 A1 | 5/1981 |
| EP | 0376839 A1 | 7/1990 |
| JP | H09504689 A | 5/1997 |
| JP | 2010524847 A | 7/2010 |
| JP | 2012530105 A | 11/2012 |
| JP | 2015510941 A | 4/2015 |
| JP | 2015-516391 A1 | 6/2015 |
| JP | 2015516391 A | 6/2015 |
| WO | 2002083182 A2 | 10/2002 |
| WO | 2009072726 A1 | 6/2009 |
| WO | 2010/129681 A1 | 11/2010 |
| WO | 2011022462 A2 | 2/2011 |
| WO | 2012/0019086 A2 | 2/2012 |
| WO | 2013/155103 A1 | 10/2013 |

OTHER PUBLICATIONS

Chinese Application No. CN201980058427.8, Office Action dated Jun. 21, 2023.
Japanese Application No. 2021-512444, Office Action dated Jun. 6, 2023.
Chinese Application No. 2019800584278 Search Report.
Kirkham, David L., "Neural stem cells from protein tyrosine phosphatase sigma knockout mice generate an altered neuronal phenotype in culture", BMC Neuroscience 2006, 7:50, Jun. 19, 2006.
Applicant: Case Western Reserve University; "Compositions and Methods for Treating Alzheimer's Desease"; European Patent Application No. EP18813399; EESR; Mar. 8, 2021; 9 pgs.
F. Jeppsson, et al.; "Discovery of AZD3839, a Potent and Selective BACE1 Inhibitor Clinical Candidate for the Treatment of Alzheimer Disease", Journal of Biological Chemistry, vol. 287, No. 49, Nov. 30, 2012, p. 41245-41257, XP055299016, ISSN: 0021-9258, DOI: 10.1074/jbc.M112.409110.
Gu, et al.; "Alzheimer's disease pathogenesis is dependent on neuronal receptor??? s"; bioRxiv; 58 pp.; Retrieved Apr. 22, 2021, 2016; doi: https://doi.org/10.1101/079806.
Japanese Office Action; Japanese Application No. 2019-565526; Apr. 23, 2021; 5 pgs.
Melanie J. Chagnon, et al.; "Functional Significance of the LAR Receptor Protein Tyrosine Phosphatase Family in Development and Diseases"; Biochemistry and Cell Biology. Biochimie Et Biologie Cellulaire; vol. 82, No. 6; Dec. 1, 2004; pp. 664-675, XP055769264, CA; ISSN: 0829-8211, DOI: 10.1139/P04-120.
Melnikova Tatiana, et al.; G-Secretase Modulator Enhances the AB-Lowering Effect of BACE1 Inhibitor in Mouse Models of Alzheimer's Disease, Alzheimer's & Dementia: the Journal of the Alzheimer's Association, vol. 12, No. 7, Oct. 1, 2016, XP029763344, ISSN: 1552-5260, DOI: 10.1016/J. JALZ.2016.06.719.

(Continued)

*Primary Examiner* — Michelle F. Paguio Frising
(74) *Attorney, Agent, or Firm* — Tarolli, Sundheim, Covell & Tummino LLP

(57) ABSTRACT

A method of promoting compensatory plasticity of spared neural cells after a neural injury includes contacting the spared neural cells with an effective amount of a therapeutic agent comprising a therapeutic peptide, wherein the therapeutic peptide comprises an amino acid sequence with at least 70% identity to SEQ ID NO:32.

27 Claims, 18 Drawing Sheets

Specification includes a Sequence Listing.

(56) References Cited

OTHER PUBLICATIONS

Russo, Alberto, et al.; "Pharmacokinetic/Pharmacodynamic Modeling of CSF AB1-40 Reduction in an Early Alzheimer's Disease Study of JNJ-54861911, an Oral Bace1 Inhibitor", Alzheimer's & Dementia: The Journal of the Alzheimer's Association, vol. 12, No. 7, Jan. 1, 2016, XPO029769823, ISSN: 1552-5260, DOI: 10.1016/J.JALZ.2016.06.1215.

Aricescu, A. Radu, et al., "Heparan Sulfate Proteoglycans Are Ligands for Receptor Protein Tyrosine Phosphatase p", Molecular and Cellular Biology, Mar. 2002, p. 1881-1892, vol. 22, No. 6.

Brown, Joshua M., et al., "A sulfated carbohydrate epitope inhibits axon regeneration after injury", PNAS, Mar. 27, 2012, vol. 109, No. 13, pp. 4768-4773.

Carey, D.M., et al., "Association of Cell Surface Heparan Sulfate Proteoglycans of Schwann Cells with Extracellular Matrix Proteins", J. Biol. Chem, 1990, 265L20627-20633.

Coles, Charlotte, et al. Proteoglycan-Specific Molecular Switch for RPTPcr Clustering and Neuronal Extension, Science. Apr. 2, 2011, 332(6028): 484-488.

Cortes, Mauricio, et al., "Sulfation if Chondroitin Sulfate Proteoglycans is necessary for proper Indian hedgehot signaling in the developing growth plate", Development 136, 1697-1706 (2009).

Dickendesher, Travis, L., "NgR1 and NgR3 are Receptors for Chondroitin Sulfate Proteoglycans", Nat. Neurosci.; 15(5): 703-712, (2012).

Examiner's Report for Canadian for Application No. 2,870,155, dated Nov. 27, 2018.

Extended European Search Report dated Oct. 30, 2015, for EP 18813399.5.

Fassler & Cooper, "BLAST Glossary," created Jul. 14, 2011, pp. 1-9, downloaded on Mar. 18, 2017 from www.ncbi.nim.nih.gov/books/NBK62051/.

Fisher Daniel, et al., "LAR is a functional receptor for CSPG Axon Growth Inhibitors", J. Neurosci. Oct. 5, 2011; 31 (40): 14051-14066.

Horn, Kevin, et al., "Another barrier to regeneration in the CNS: Activated macrophages induce extensive retraction of dystrophic axons through direct physical interactions", J. Neurosci. Sep. 17, 2008; 28(38):9330-9341.

Patel, et al., "Inhibition of the protein tyrosine phosphatase PTP1B: Potential therapy for obesity, insulin resistance and type-2 diabetes mellitus", World Journal of Pharmacy and Pharmaceutical Science, vol. 4, Issue 9, pp. 347-354.

Majeti, Ravindra, et al., "Dimerization-Induced Inhibition of Receptor Protein Tyrosine Phosphatase Function Through an Inhibitory Wedge", Science vol. 279, Jan. 2, 1998.

Office Action for Japanese Patent Application No. 2015-505856, dated Jan. 5, 2017.

Office action for Japanese Patent Application No. 2015-505856, dated Oct. 3, 2017.

Shen, Yingjie, et al., "PTPo is a Receptor for Chondroitin Sulfate Proteoglycan, an Inhibitor of Neural Regeneration", Science. Oct. 23, 2009; 326(5952: 592-596).

Tom, Veronica J., et al., "Studies in the Development and Behavior of the Dystrophic Growth Cone, the Hallark of Regeneration Failure, and an In Vitro Model of the Glial Scar and after Spinal Injury", The journal of Neuroscience, Jul. 21, 2004, 24 (29):6531-6539.

Xie, Youmei, et al., "Protein-Tyrosine Phosphatase (PTP) Wedge Domain Peptides: A Novel Approach for Inhibition of PTP Function and Augmentation of Protein-Tyrosine Kinase Function", J. Biol. Chem. 2006, 281-16482-16492.

Zipes "Influence of Myocardial Ischemia and Infarction on Autonomic Innervation of Heart," Circulation. 1990;82-1095-1105 (Year: 1990).

Applicant: Case Western Reserve University; "Methods and Compositions for Inducing Neural Plasticity"; European Application No. EP19857885; Extended European Search Report; May 11, 2022; 7 pgs.

Japanese Application No. 2020-133525; Japanese office Action dated Mar. 22, 2022; 6 pgs.

Jiang, Guoqiang, et al. "Dimerization inhibits the activity of receptor-like protein-tyrosine phosphatase-a." Nature 401.6753 (1999): 606-610.

Applicant: Case Western Reserve University; "Compositions and Methods for Treating Alzheimer's Disease"; Chinese Application No. 201880036972.2; Chinese First Office Action dated Nov. 2, 2022, 14 pgs.

Harlow, Danielle E., and Wendy B. Macklin. "Inhibitors of myelination: ECM changes, CSPGs and PTPs." Experimental neurology 251 (2014): 39-46.

Japanese Application No. 2019-571337; Japanese Office Action dated Aug. 2, 2022, 9 pgs.

Jerry Silver, "Compositions and Methods for Treating Myelin Disorders"; U.S. Appl. No. 16/630,271, filed Jan. 10, 2020; Final Office Action dated Oct. 24, 2022; 21 pgs.

Applicant: Case Western Reserve University; "Compositions and Methods for Treating Myelin Disorders"; European Patent Application No. 18832119.4; Extended European Search Report; May 26, 2021; 10 pgs.

Li Heng et al; "Enhanced Regeneration and Functional Recovery After Spinal Root Avulsion by Manipulation of the Proteoglycan Receptor PTP [sigma]"; Scientific Reports, vol. 5, No. 1, Oct. 14, 2015; XP055778445, DOI: 10.1038/srep14923 Retrieved from the Internet: URL:HTTP://www.nature.com/articles/srep14923.

Motavaf Mahsa, et al; "Attempts to Overcome Remyelination Failure: Toward Opening New Therapeutic Avenues for Multiple Sclerosis"; Cellular and Molecular Neurobiology, Springer New York, US, vol. 37, No. 8, Feb. 21, 2019, pp. 1335-1348, XPO36333800, ISSN: 0272-4340, DOI: 10.1007/S10571-017-0472-6.

Chinese Application No. 201980058427.8, Decision of Rejection dated Jun. 29, 2024.

Australian Application No. 2019334965, Examination Report dated Sep. 12, 2024.

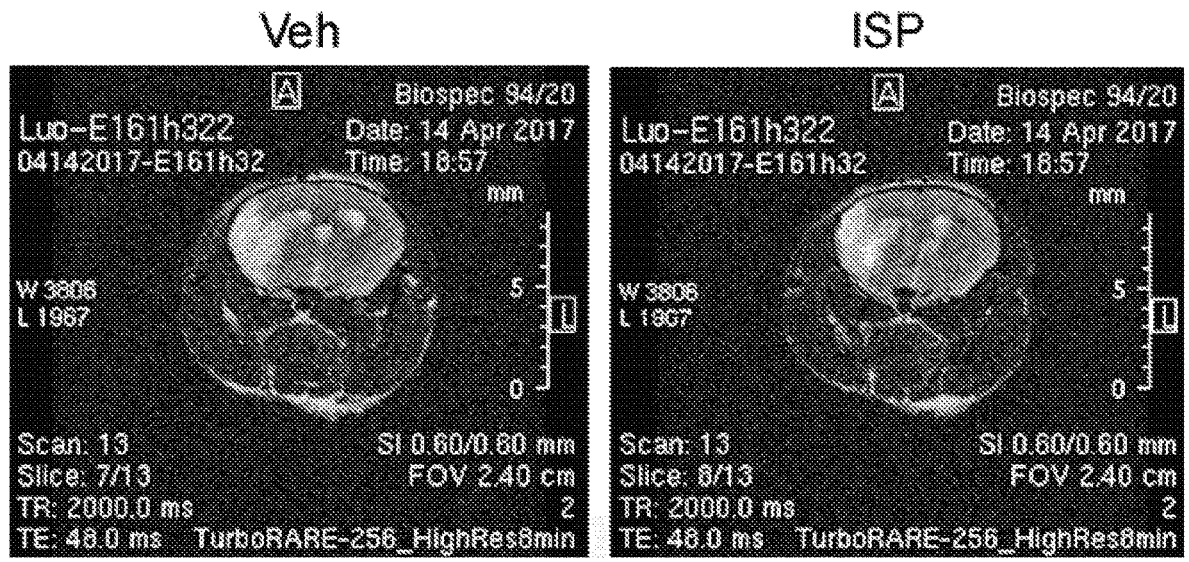
*FIG. 2A*
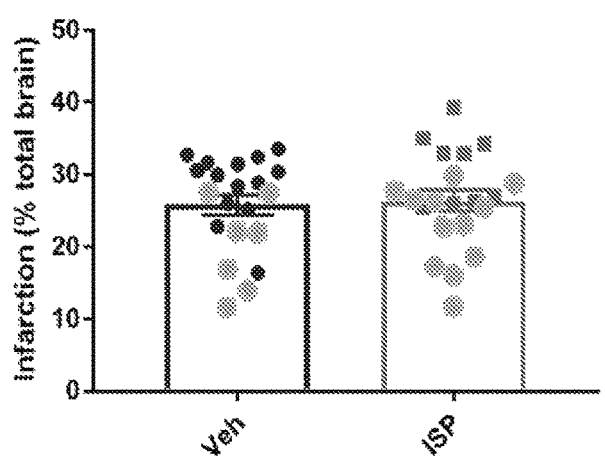
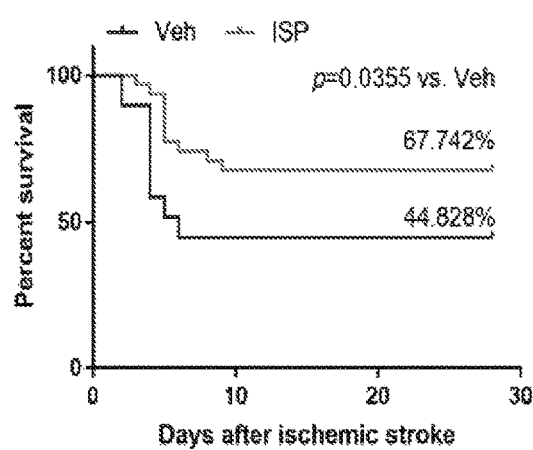
*FIG. 2B*        *FIG. 2C*

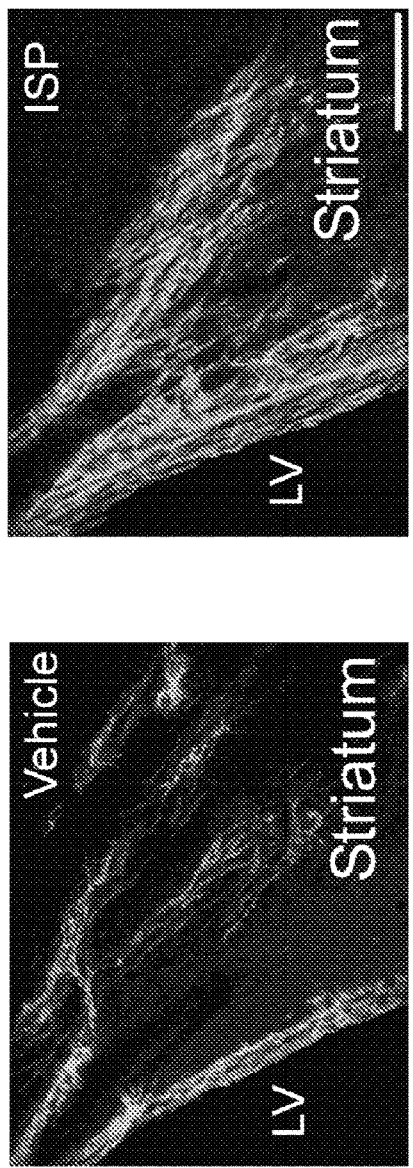
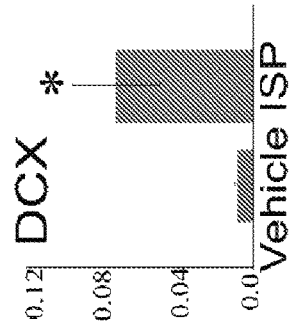
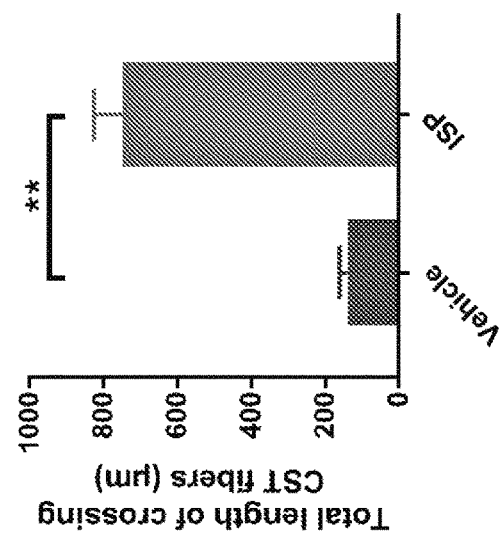
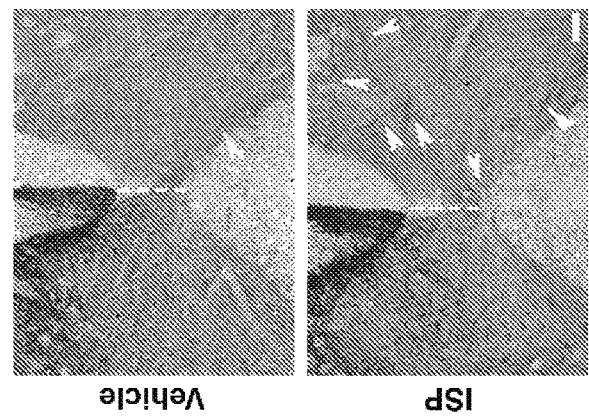
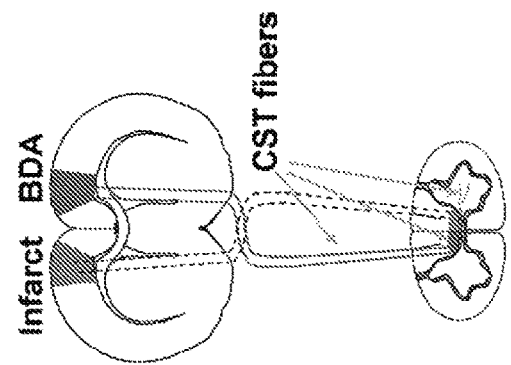
FIG. 7A FIG. 7B FIG. 7C FIG. 7D FIG. 7E FIG. 7F

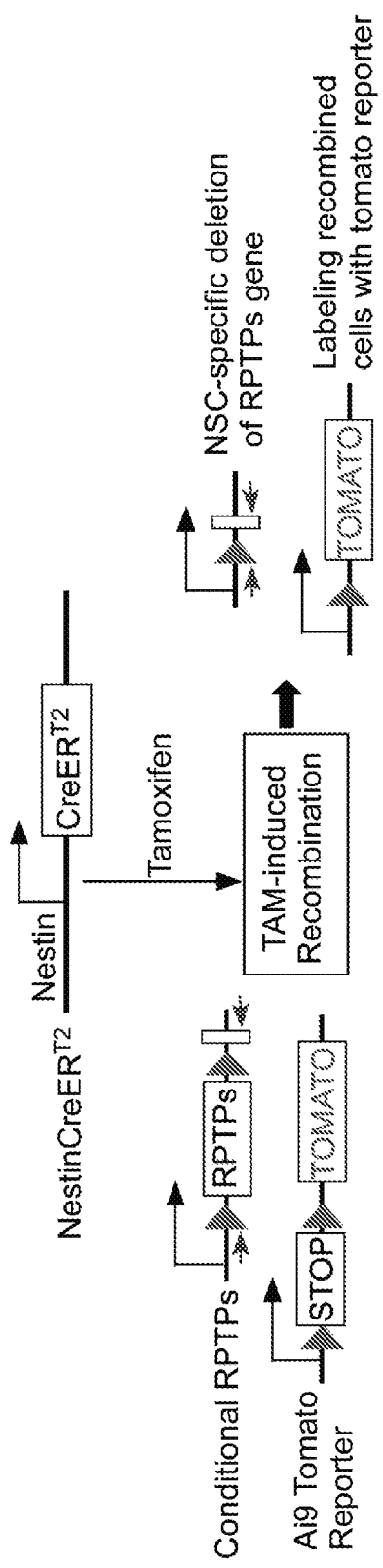
*FIG. 8A*
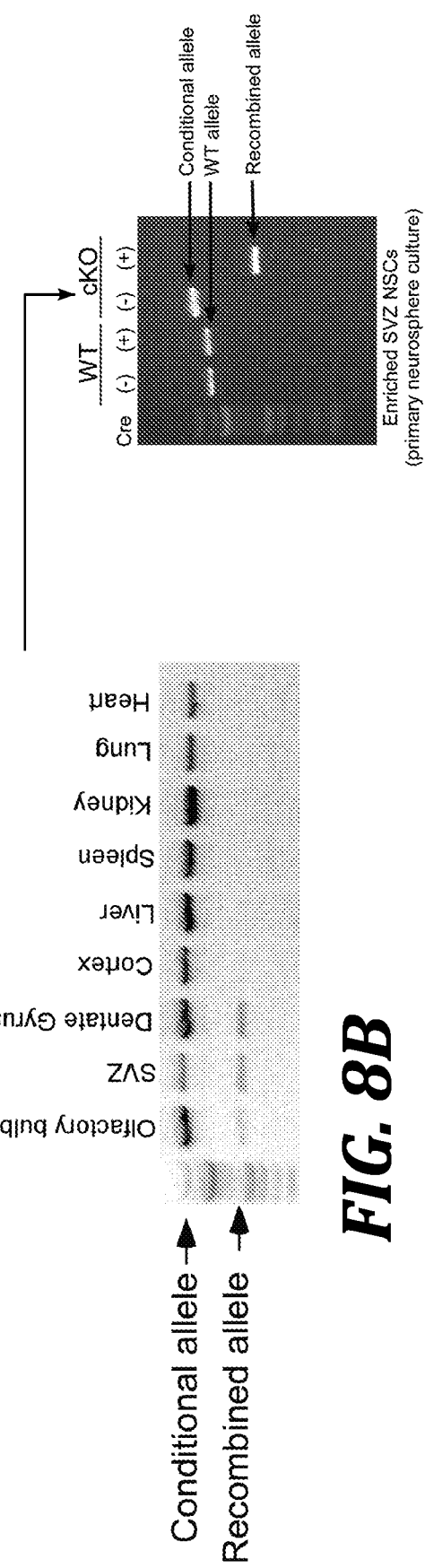
*FIG. 8B*
*FIG. 8C*

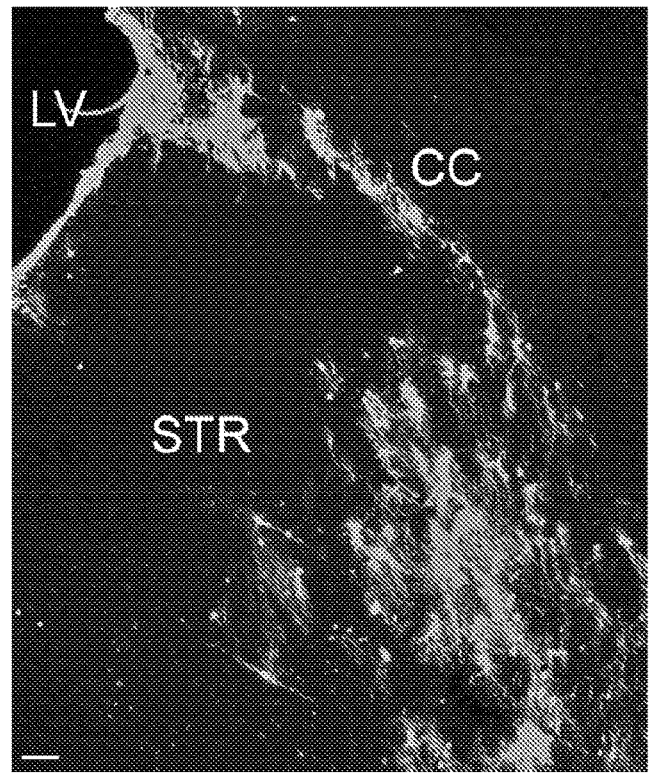
FIG. 8D
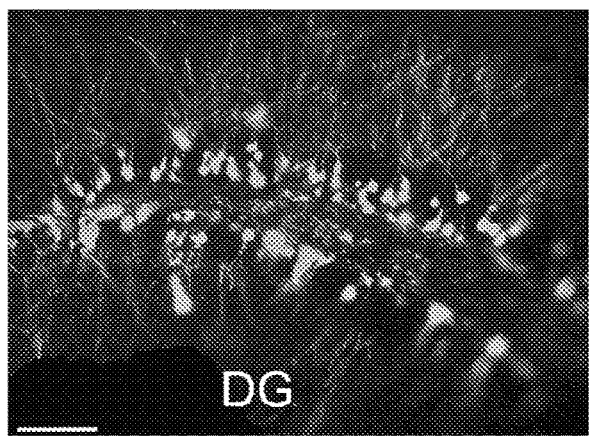 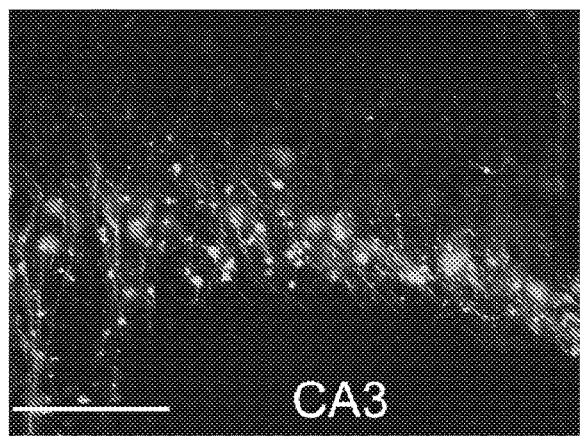
FIG. 8E          FIG. 8F

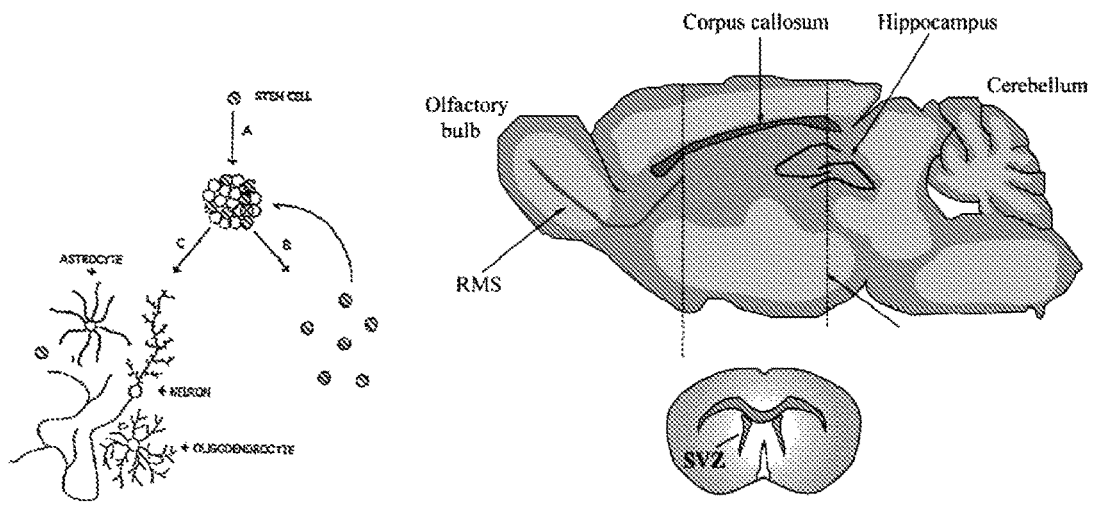
FIG. 10A
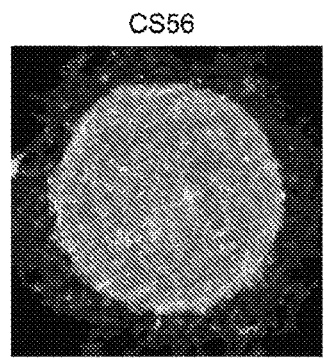 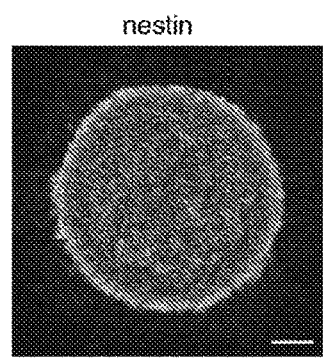
FIG. 10B  FIG. 10C
 
FIG. 10D  FIG. 10E

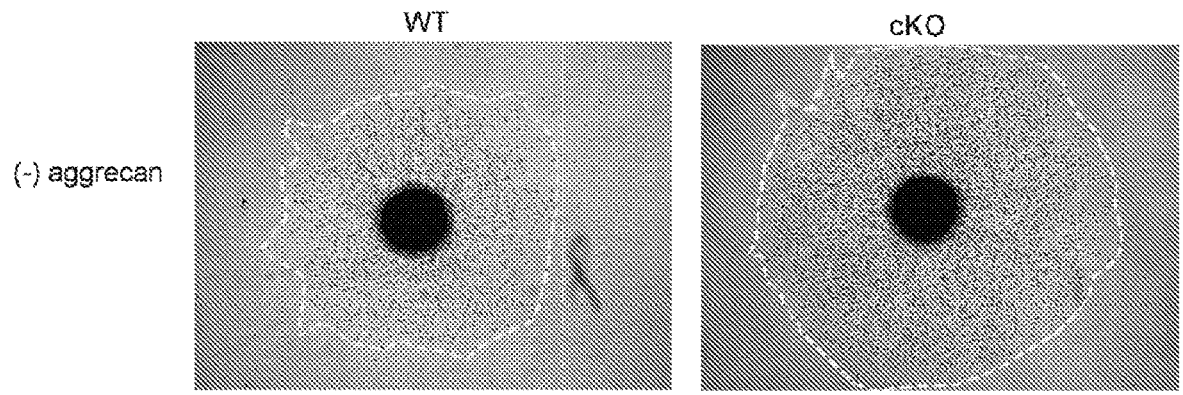
FIG. 11A  FIG. 11B
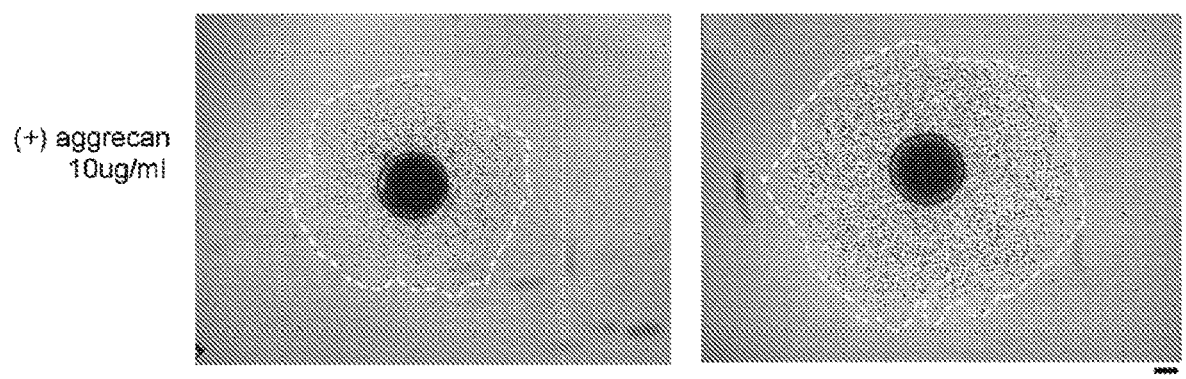
FIG. 11C  FIG. 11D
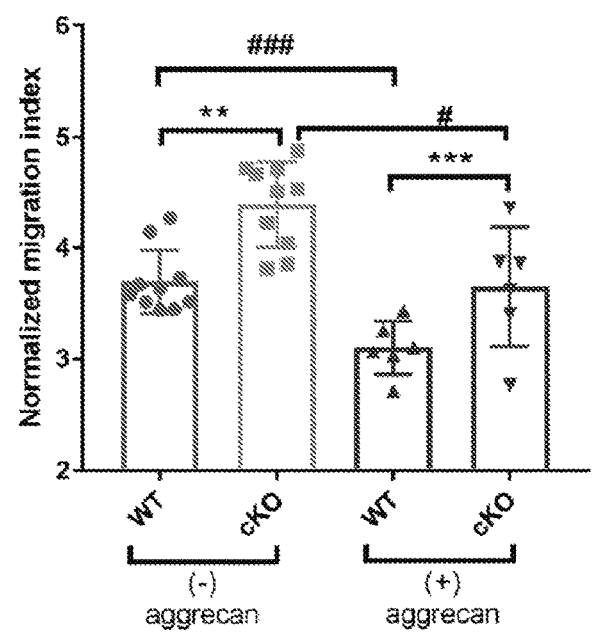
FIG. 11E

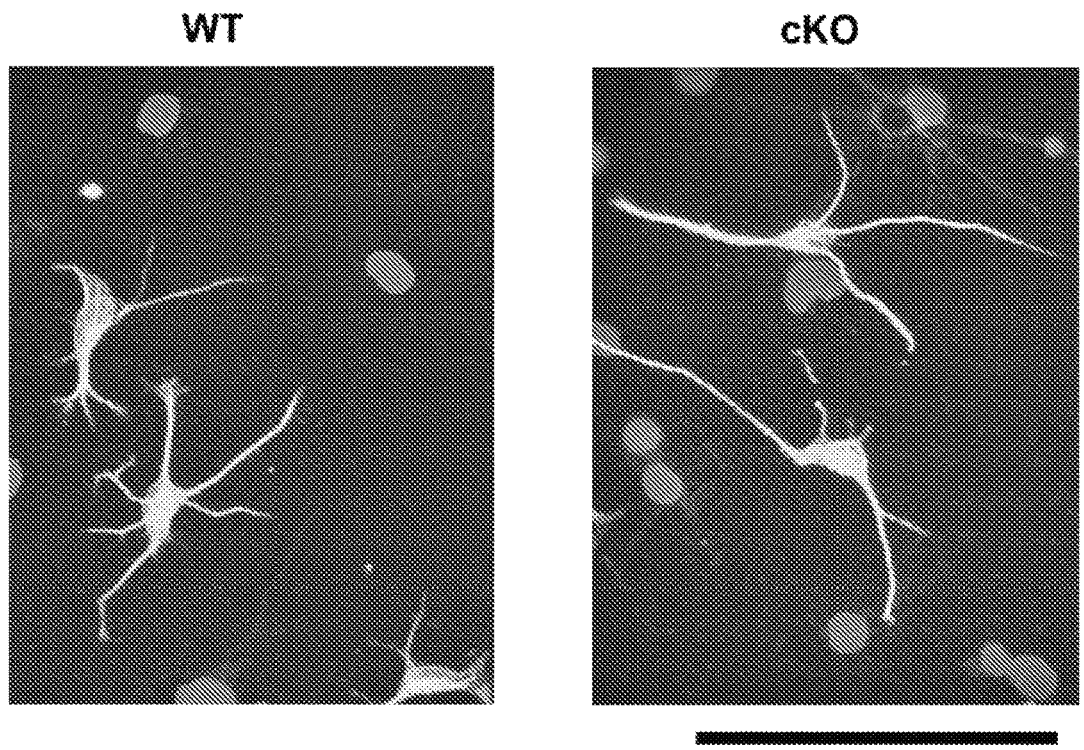
*FIG. 13A*    *FIG. 13B*
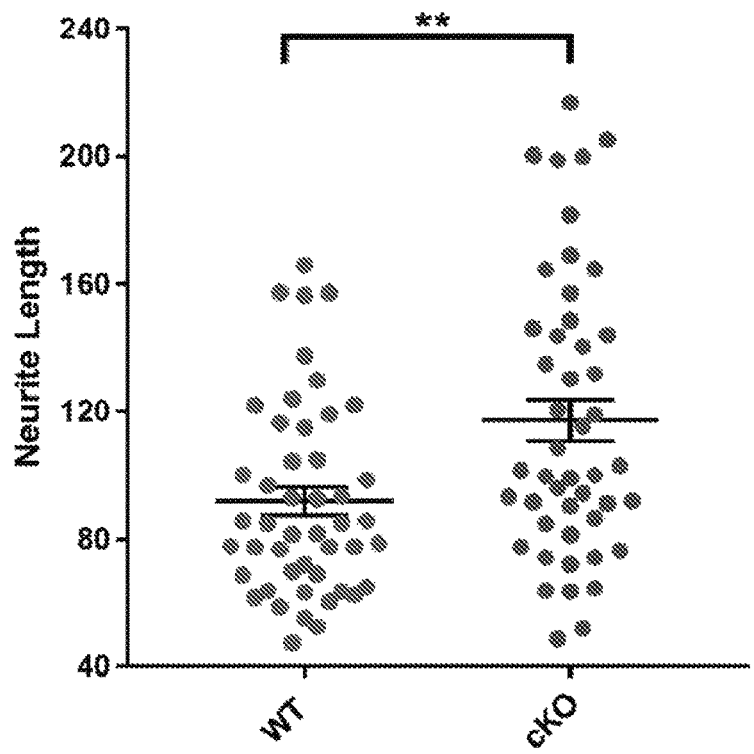
*FIG. 13C*

SEQUENCE LISTING

```
<160> NUMBER OF SEQ ID NOS: 63

<210> SEQ ID NO 1
<211> LENGTH: 22
<212> TYPE: PRT
<213> ORGANISM: Xenopus borealis

<400> SEQUENCE: 1

Asp Leu Ala Glu His Thr Glu His Leu Lys Ala Asn Asp Asn Leu Lys
1               5                   10                  15

Ser Gln Glu Tyr Glu Ser
            20

<210> SEQ ID NO 2
<211> LENGTH: 21
<212> TYPE: PRT
<213> ORGANISM: Anolis carolinensis

<400> SEQUENCE: 2

Asp His Thr Glu His Leu Lys Ala Asn Asp Asn Leu Lys Leu Ser Gln
1               5                   10                  15

Glu Tyr Glu Ser Ile
            20

<210> SEQ ID NO 3
<211> LENGTH: 24
<212> TYPE: PRT
<213> ORGANISM: Danio rerio

<400> SEQUENCE: 3

Glu Leu Ala Glu His Thr Glu Leu Leu Lys Ala Asn Asp Asn Leu Lys
1               5                   10                  15

Leu Ser Gln Glu Tyr Glu Ser Ile
```

```
<210> SEQ ID NO 4
<211> LENGTH: 24
<212> TYPE: PRT
<213> ORGANISM: Oreochromis aureus

<400> SEQUENCE: 4

Glu Leu Ala Glu His Thr Glu Leu Leu Lys Ala Asn Asp Asn Leu Lys
1               5                   10                  15

Leu Ser Gln Glu Tyr Glu Ser Ile
            20

<210> SEQ ID NO 5
<211> LENGTH: 24
<212> TYPE: PRT
<213> ORGANISM: Gallus gallus

<400> SEQUENCE: 5

Glu Leu Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 6
<211> LENGTH: 24
<212> TYPE: PRT
<213> ORGANISM: Fringilla coelebs

<400> SEQUENCE: 6

Glu Leu Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 7
<211> LENGTH: 24
<212> TYPE: PRT
<213> ORGANISM: Ornithorhynchus anatinus

<400> SEQUENCE: 7

Glu Leu Ala Glu His Thr Asp His Leu Lys Ala Asn Asp Asn Leu Lys
1               5                   10                  15

Leu Ser Gln Glu Tyr Glu Ser Ile
            20

<210> SEQ ID NO 8
<211> LENGTH: 24
<212> TYPE: PRT
<213> ORGANISM: Sarcophilus harrisii

<400> SEQUENCE: 8

Glu Met Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 9
<211> LENGTH: 24
<212> TYPE: PRT
<213> ORGANISM: Mustela putorius

<400> SEQUENCE: 9
```

```
<210> SEQ ID NO 9 (continued)
```

Asp Met Ala Glu His Thr Glu Arg Leu Lys Ala Asn Asp Ser Leu Lys
1               5                   10                  15

Leu Ser Gln Glu Tyr Glu Ser Ile
            20

```
<210> SEQ ID NO 10
<211> LENGTH: 24
<212> TYPE: PRT
<213> ORGANISM: Galago alleni

<400> SEQUENCE: 10
```

Asp Met Ala Glu His Thr Glu Arg Leu Lys Ala Asn Asp Ser Leu Lys
1               5                   10                  15

Leu Ser Gln Glu Tyr Glu Ser Ile
            20

```
<210> SEQ ID NO 11
<211> LENGTH: 24
<212> TYPE: PRT
<213> ORGANISM: Callithrix aurita

<400> SEQUENCE: 11
```

Asp Met Ala Glu His Thr Glu Arg Leu Lys Ala Asn Asp Ser Leu Lys
1               5                   10                  15

Leu Ser Gln Glu Tyr Glu Ser Ile
            20

```
<210> SEQ ID NO 12
<211> LENGTH: 24
<212> TYPE: PRT
<213> ORGANISM: Rattus rattus

<400> SEQUENCE: 12
```

Asp Met Ala Glu His Thr Glu Arg Leu Lys Ala Asn Asp Ser Leu Lys
1               5                   10                  15

Leu Ser Gln Glu Tyr Glu Ser Ile
            20

```
<210> SEQ ID NO 13
<211> LENGTH: 24
<212> TYPE: PRT
<213> ORGANISM: Mus musculus

<400> SEQUENCE: 13
```

Asp Met Ala Glu His Met Glu Arg Leu Lys Ala Asn Asp Ser Leu Lys
1               5                   10                  15

Leu Ser Gln Glu Tyr Glu Ser Ile
            20

```
<210> SEQ ID NO 14
<211> LENGTH: 24
<212> TYPE: PRT
<213> ORGANISM: Canis familiaris

<400> SEQUENCE: 14
```

Asp Met Ala Glu His Thr Glu Arg Leu Lys Ala Asn Asp Ser Leu Lys
1               5                   10                  15

Leu Ser Gln Glu Tyr Glu Ser Ile
            20

```
<210> SEQ ID NO 15
```

```
<211> LENGTH: 24
<212> TYPE: PRT
<213> ORGANISM: Sus barbatus

<400> SEQUENCE: 15

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 16
<211> LENGTH: 24
<212> TYPE: PRT
<213> ORGANISM: Bos primigenius

<400> SEQUENCE: 16

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 17
<211> LENGTH: 24
<212> TYPE: PRT
<213> ORGANISM: Ovis aries

<400> SEQUENCE: 17

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 18
<211> LENGTH: 24
<212> TYPE: PRT
<213> ORGANISM: Orcinus orca

<400> SEQUENCE: 18

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 19
<211> LENGTH: 24
<212> TYPE: PRT
<213> ORGANISM: Saimiri sciureus

<400> SEQUENCE: 19

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 20
<211> LENGTH: 24
<212> TYPE: PRT
<213> ORGANISM: Papio hamadryas

<400> SEQUENCE: 20

Asp Met Ala Glu His Thr Glu Arg Leu Lys Ala Asn Asp Ser Leu Lys
1               5                   10                  15
```

Leu Ser Gln Glu Tyr Glu Ser Ile
            20

<210> SEQ ID NO 21
<211> LENGTH: 24
<212> TYPE: PRT
<213> ORGANISM: Gorilla gorilla

<400> SEQUENCE: 21

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 22
<211> LENGTH: 24
<212> TYPE: PRT
<213> ORGANISM: Hylobates lar

<400> SEQUENCE: 22

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 23
<211> LENGTH: 24
<212> TYPE: PRT
<213> ORGANISM: Macaca radiata

<400> SEQUENCE: 23

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 24
<211> LENGTH: 24
<212> TYPE: PRT
<213> ORGANISM: Pan troglodytes

<400> SEQUENCE: 24

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 25
<211> LENGTH: 24
<212> TYPE: PRT
<213> ORGANISM: Homo sapiens

<400> SEQUENCE: 25

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 26
<211> LENGTH: 24
<212> TYPE: PRT
<213> ORGANISM: Rattus rattus

<400> SEQUENCE: 26

Asp Leu Ala Asp Asn Ile Glu Arg Leu Lys Ala Asn Asp Gly Leu Lys
1               5                   10                  15

Phe Ser Gln Glu Tyr Glu Ser Ile
            20

<210> SEQ ID NO 27
<211> LENGTH: 24
<212> TYPE: PRT
<213> ORGANISM: Rattus rattus

<400> SEQUENCE: 27

Glu Leu Ala Asp His Ile Glu Arg Leu Lys Ala Asn Asp Asn Leu Lys
1               5                   10                  15

Phe Ser Gln Glu Tyr Glu Ser Ile
            20

<210> SEQ ID NO 28
<211> LENGTH: 24
<212> TYPE: PRT
<213> ORGANISM: Rattus rattus

<400> SEQUENCE: 28

Lys Leu Glu Glu Glu Ile Asn Arg Arg Met Ala Asp Asp Asn Lys Ile
1               5                   10                  15

Phe Arg Glu Glu Phe Asn Ala Leu
            20

<210> SEQ ID NO 29
<211> LENGTH: 10
<212> TYPE: PRT
<213> ORGANISM: Homo sapiens

<400> SEQUENCE: 29

Asp Met Ala Glu His Thr Glu Arg Leu Lys
1               5                   10

<210> SEQ ID NO 30
<211> LENGTH: 4
<212> TYPE: PRT
<213> ORGANISM: Homo sapiens

<400> SEQUENCE: 30

Ala Asn Asp Ser
1

<210> SEQ ID NO 31
<211> LENGTH: 10
<212> TYPE: PRT
<213> ORGANISM: Homo sapiens

<400> SEQUENCE: 31

Leu Lys Leu Ser Gln Glu Tyr Glu Ser Ile
1               5                   10

<210> SEQ ID NO 32
<211> LENGTH: 14
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Xaa is T or M

<400> SEQUENCE: 32

Glu His Xaa Glu Arg Leu Lys Ala Asn Asp Ser Leu Lys Leu
1               5                   10

<210> SEQ ID NO 33
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Xaa is any amino acid residue

<400> SEQUENCE: 33

Asp Met Ala Glu His Xaa Glu Arg Leu Lys Ala Asn Asp Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Gly Arg Lys Lys Arg Arg Gln Arg Arg Arg
1               5                   10

<210> SEQ ID NO 35
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa isany amino acid residue

<400> SEQUENCE: 35

Gly Arg Lys Lys Arg Arg Gln Arg Arg Arg Xaa Asp Leu Ala Glu His
1               5                   10                  15

Thr Glu His Leu Lys Ala Asn Asp Asn Leu Lys Ser Gln Glu Tyr Glu
                20                  25                  30

Ser

<210> SEQ ID NO 36
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 36

Gly Arg Lys Lys Arg Arg Gln Arg Arg Arg Xaa Asp His Thr Glu His
1               5                   10                  15

Leu Lys Ala Asn Asp Asn Leu Lys Leu Ser Gln Glu Tyr Glu Ser Ile
                20                  25                  30

<210> SEQ ID NO 37
<211> LENGTH: 35
<212> TYPE: PRT

<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 37

```
Gly Arg Lys Lys Arg Arg Gln Arg Arg Arg Xaa Glu Leu Ala Glu His
1               5                   10                  15

Thr Glu Leu Leu Lys Ala Asn Asp Asn Leu Lys Leu Ser Gln Glu Tyr
            20                  25                  30

Glu Ser Ile
        35
```

<210> SEQ ID NO 38
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 38

```
Gly Arg Lys Lys Arg Arg Gln Arg Arg Arg Xaa Glu Leu Ala Glu His
1               5                   10                  15

Thr Glu Leu Leu Lys Ala Asn Asp Asn Leu Lys Leu Ser Gln Glu Tyr
            20                  25                  30

Glu Ser Ile
        35
```

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 39

```
Gly Arg Lys Lys Arg Arg Gln Arg Arg Arg Xaa Glu Leu Ala Glu His
1               5                   10                  15

Thr Glu His Leu Lys Ala Asn Asp Asn Leu Lys Leu Ser Gln Glu Tyr
            20                  25                  30

Glu Ser Ile
        35
```

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 40

Gly Arg Lys Lys Arg Arg Gln Arg Arg Xaa Glu Leu Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 41

Gly Arg Lys Lys Arg Arg Gln Arg Arg Xaa Glu Leu Ala Glu His
1               5                   10                  15

Thr Asp His Leu Lys Ala Asn Asp Asn Leu Lys Leu Ser Gln Glu Tyr
            20                  25                  30

Glu Ser Ile
        35

<210> SEQ ID NO 42
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 42

Gly Arg Lys Lys Arg Arg Gln Arg Arg Xaa Glu Met Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 43
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 43

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

```
<210> SEQ ID NO 44
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 44

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 45
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: Xaa can be any naturally occurring amino acid

<400> SEQUENCE: 45

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 46
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 46

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 47
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue
```

-continued

```
<400> SEQUENCE: 47

Gly Arg Lys Lys Arg Arg Gln Arg Arg Xaa Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile
        35

<210> SEQ ID NO 48
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 48

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 49
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid

<400> SEQUENCE: 49

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 50
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 50

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
```

```
<210> SEQ ID NO 51
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: Xaa can be any naturally occurring amino acid

<400> SEQUENCE: 51

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 52
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 52

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 53
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 53

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 54
<211> LENGTH: 35
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (11)..(11)
<223> OTHER INFORMATION: Xaa can be any naturally occurring amino acid

<400> SEQUENCE: 54

Gly Arg Lys Lys Arg Arg Gln Arg Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 55
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 55

Gly Arg Lys Lys Arg Arg Gln Arg Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 56
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 56

Gly Arg Lys Lys Arg Arg Gln Arg Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 57
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 57

Gly Arg Lys Lys Arg Arg Gln Arg Arg Arg Xaa Asp Met Ala Glu His
1               5                   10                  15

Thr Glu Arg Leu Lys Ala Asn Asp Ser Leu Lys Leu Ser Gln Glu Tyr
```

-continued

```
                    20                  25                  30

Glu Ser Ile
        35

<210> SEQ ID NO 58
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 58

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 59
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue

<400> SEQUENCE: 59

Gly Arg Lys Lys Arg Arg Gln Arg Arg Xaa Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 60
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue
<220> FEATURE:
<221> NAME/KEY: MOD_RES
<222> LOCATION: (14)..(14)
<223> OTHER INFORMATION: Xaa is any amino acid residue

<400> SEQUENCE: 60

Gly Arg Lys Lys Arg Arg Gln Arg Arg Xaa Glu His Xaa Glu Arg
1               5                   10                  15

Leu Lys Ala Asn Asp Ser Leu Lys Leu
            20                  25

<210> SEQ ID NO 61
<211> LENGTH: 25
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is any amino acid residue
<220> FEATURE:
<221> NAME/KEY: MOD_RES
<222> LOCATION: (17)..(17)
<223> OTHER INFORMATION: Xaa is any amino acid residue

<400> SEQUENCE: 61

Gly Arg Lys Lys Arg Arg Gln Arg Arg Xaa Asp Met Ala Glu His
1               5                   10                  15

Xaa Glu Arg Leu Lys Ala Asn Asp Ser
            20                  25

<210> SEQ ID NO 62
<211> LENGTH: 35
<212> TYPE: PRT
<213> ORGANISM: Artificial Sequence
<220> FEATURE:
<223> OTHER INFORMATION: Synthetic Construct

<400> SEQUENCE: 62

Gly Arg Lys Lys Arg Arg Gln Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile
        35

<210> SEQ ID NO 63
<211> LENGTH: 35
<212> TYPE: PRT
<213> ORGANISM: Artificial Sequence
<220> FEATURE:
<223> OTHER INFORMATION: Synthetic Construct

<400> SEQUENCE: 63

Gly Arg Lys Lys Arg Arg Gln Arg Arg Cys Ile Arg Glu Asp Asp
1               5                   10                  15

Ser Leu Met Leu Tyr Ala Leu Ala Gln Glu Lys Lys Glu Ser Asn Met
            20                  25                  30

His Glu Ser
        35
```

METHODS AND COMPOSITIONS FOR INDUCING NEURAL PLASTICITY

CROSS-REFERENCE(S) TO RELATED APPLICATION

This application claims the benefit of U.S. Provisional Application No. 62/727,420, filed Sep. 5, 2018, the disclosure of which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is CWR026868WOORD.txt. The text file is 24,598 bytes; was created on Aug. 28, 2019; and is being submitted via EFS-Web with the filing of the specification.

BACKGROUND

Neural injuries result in dysfunction or death of neural tissues, manifesting a wide variety of symptoms and effects. The injuries can be caused by external events, such as traumatic brain injuries or ischemic conditions, from internal events, such as stroke, aneurysm, cerebral hemorrhage, thrombus, or embolism, or from more chronic neurodegenerative diseases, such as multiple sclerosis.

As an illustrative example, stroke occurs when there is an interruption of blood flow to the brain, causing the death of neural tissue and focal neurological deficits. The signs and symptoms may vary with the location and extent of the stroke. There are nearly 800,000 strokes of all types per year in the United States, and ischemic strokes account for approximately 80% of these strokes. Roger et al. (2011) Circulation 123(4):e18-e209. In Europe, the estimated annual incident of stroke is over 1.1 million, with a similar percentage of these, approximately 80%, being ischemic strokes. Heuschmann et al. (2009) Stroke 40(5):1557-1563.

Guidelines for the evaluation and treatment of acute stroke patients focus on reperfusion therapies and factors that may exacerbate stroke or complicate clinical course. The diagnosis of acute ischemic stroke is made through a combination of a history and physical examination that is consistent with focal ischemia and a resulting neurological deficit. Brain imaging, either computed tomography (CT) or magnetic resonance imaging (MRI) is used to exclude hemorrhage and other focal pathologies and document early signs of ischemia.

Stroke can also be viewed as a chronic disease. The manifestations of chronic stroke disease include cognitive deficits, dysphagia and gait disorder, which the acute exacerbations can take the form of decompensations in swallow or gait, or a delirium. As with all chronic disease, the risk of further acute stroke is higher with patients of chronic stroke disease; with the risk or recurrent stroke about six times greater than the risk of the first ever stroke in a general population of same age and sex.

Many therapeutic approaches to neural injury address restorative strategies to regain function of injured neurons. However, the window of time to intervene prior to total loss of function and/or neural death is short. Accordingly, despite the advances in the art in addressing many neural injuries a need remains for effective and flexible treatments to regain function and/or ameliorate negative impacts after a neural injury. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

This disclosure generally relates to agents, compounds, and methods of treating neural injury, such as neural injury caused by traumatic brain injury (TBI), ischemia, stroke (e.g., ischemic stroke, and/or chronic stroke disease), aneurysm, cerebral hemorrhage, thrombus, embolism, multiple sclerosis (MS), or Alzheimer's disease in a subject in need thereof, as well as to methods for the treatment of diseases or disorders associated with glial scar formation and/or chondroitin sulfate proteoglycan (CSPG) in the nervous system of subjects In one aspect, the disclosure provides a method of promoting compensatory plasticity of spared neural cells after a neural injury. The method comprises contacting the spared neural cells with an effective amount of a therapeutic agent that inhibits one or more of catalytic activity, signaling, or function of PTPσ in the spared neural cells. In some embodiments, the therapeutic agent comprises a therapeutic peptide, wherein the therapeutic peptide comprises an amino acid sequence with at least 70% identity to SEQ ID NO: 32 or at least 70% identity to SEQ ID NO: 33.

In another aspect, the disclosure provides a method of treating a neural injury in a subject. The method comprises promoting compensatory plasticity of spared neural cells after the neural injury by administering to the subject an effective amount of a therapeutic agent comprising a therapeutic peptide, wherein the therapeutic peptide comprises an amino acid sequence with at least 70% identity to SEQ ID NO: 32 or at least 70% identity to SEQ ID NO: 33.

In various embodiments of these aspects, the spared neural cells can be neural stem cells, can comprise oligodendrocyte progenitor cells (OPCs) and/or glial precursor cells (GPCs), or can be neurons. In some embodiments, the compensatory plasticity can manifest in neurite outgrowth of the spared neural cells, such as axonal sprouting or dendrite sprouting or branching. In some embodiments, the compensatory plasticity can manifest in compensatory migration of spared neural cells toward the neural injury. In some embodiments, the neural injury is in the central nervous system, such as the brain. In some embodiments, the neural injury is caused by traumatic brain injury (TBI), multiple sclerosis (MS), Alzheimer's disease, ischemia, stroke, aneurysm, cerebral hemorrhage, thrombus, or embolism.

In some embodiments, the therapeutic agent further comprises a transport moiety linked to the therapeutic peptide and facilitates uptake of the therapeutic peptide by a cell. In some embodiments, the transport moiety is an HIV Tat transport moiety. In some embodiments, the therapeutic agent is administered systemically, intrathecally, or intravitreally to the subject.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2A-2C: FIG. 2A illustrates T2-weighted MRI scan images and FIG. 2B illustrates a graph showing vehicle and ISP treatment groups have the same infarct size at 18 hours—post stroke, induced by transient proximal middle cerebral artery occlusion (tMCAO) surgery, before the treatment starts at 24 hours post-stroke. FIG. 2C graphically illustrates that continuous post-stroke ISP treatment increased the survival of stroke animals (67.742%) over time versus vehicle treated stroke animals (44.828%) over time.

FIGS. 7A-7F illustrate that ISP treatment enhances both neuroblast cell formation and cortical spinal tract axonal sprouting. FIGS. 7A-7C are images and a graph demonstrating that post-stroke ISP treatment enhanced DCX+neuroblasts in post-stroke mice both near the lateral ventricle and adjacent striatal tissues. *p<0.05, n=4. Scale bar=100 µm. FIGS. 7D-7F are a cartoon schematic, images, and a graph, respectively, demonstrating that post-stroke ISP treatment enhances axonal sprouting from contralateral cortico-spinal tract. Crossed CST fibers at the cervical spinal cord (arrows) labeled by contralateral cortical BDA tracing. (p<0.01, Student's t-test, n=3 for each group).

FIGS. 8A-8F illustrate the generation and characterization of NSC-specific deletion of PTPσ gene and simultaneous labeling of tomato reporter in conditional (inducible) KO mice. FIG. 8A schematically illustrates the procedure to generate inducible/conditional KO (cKO) of PTPσ gene with simultaneous labeling. FIGS. 8B and 8C illustrate electrophoresis images confirming conditional and recombined alleles with or without induction. PTPσ gene recombination was observed only in adult NSCs+ niches (FIG. 8B) and enriched primary adult NSC neurospheres (FIG. 8C). FIGS. 8D-8F are images illustrating SVZ or SGZ originated adult born tomato+ cells in striatum (FIG. 8D) and DG (FIG. 8E), and their projections to CA3 area in hippocampus (FIG. 8F). Scale bar=100 µm.

FIG. 9A schematically illustrates the procedure to generate AAV mediated-adult neuronal-specific deletion of PTPσ gene and simultaneous labeling of tomato reporter in conditional PTPσ mice. FIG. 9B is an image of an exemplary electrophoresis analysis confirming conditional and recombined alleles in tissues of the subject mice. FIG. 9C is an image of induced PTPσ deletion as labeled by tomato reporter, showing tomato reporter labeling of cortical neurons (labeled as d; with a magnification in FIG. 9D) and their projections to striatum (labeled as e; with a magnification in FIG. 9E), crossing corpus callosum (labeled as f; with a magnification in FIG. 9F) to contralateral cortex (labeled as g; with a magnification in FIG. 9G). FIG. 9H illustrates the corticospinal tract (CST) and images demonstrating that tomato reporter also successfully labeled corticospinal tract (CST). Scale bar=50 µm.

FIGS. 10A-10E illustrate the establishment and characterization of adult neural stem cell cultures. FIG. 10A schematically illustrates establishment of adult neural stem cells (NSCs) culture from wt or cKO mice. FIGS. 10B and 10C are images confirming the adult NSCs produce CSPGs (FIG. 10B) and are nestin positive (FIG. 10C). FIG. 10D is an image from a gradient spot assay where wt NSCs (nestin positive; arrows) cannot penetrate the outer CSPG rim visualized by CS56 immunostaining (green). In contrast, FIG. 10E is an image showing cKO NSCs can penetrate CSPG rim demonstrating loss of PTPσ function in them. Scale bar=100 um.

FIGS. 11A-11E illustrate that aggrecan substrate coating leads to decreased migration of adult NSCs and deletion of the PTPσ gene in cKO NSC cells (compared to wt) results in enhanced migration both under basal levels (no aggrecan coating) and with aggrecan coating. FIG. 11A is a representative image of wild type NSC without aggrecan substrate coating. FIG. 11B is an image of a representative cKO NSC without aggrecan substrate coating. Considering that NSCs produce CSPGs themselves, it explains why deletion or inhibition of PTPσ enhances NSCs migration without aggrecan substrate coating. In ischemic brain, because reactive astrocytic glia produce additional CSPGs within the substrate around the lesion, the migration of NSCs in the presence of extra aggrecan substrate coating were also tested. FIG. 11C is an image of a representative wild type NSC with aggrecan substrate coating, demonstrating that extra aggrecan coating inhibited the migration of WT NSCs and deletion of PTPσ in cKO cells is able to enhance the migration of cKO cells even with extra aggrecan coating. FIG. 11D is an image of a representative cKO NSC with aggrecan substrate coating. Scale bar=50 um. Quantification of migration shown in (E).  and * indicate p<0.01 and p<0.001 compared to wt cells and # and ### indicate p<0.05 and p<0.001 compared to no aggrecan coating condition (Two way ANOVA, Tukey post hoc comparison).

FIG. 12A is a series of images showing migration of control and ISP treated cells cultured with or without aggrecan coating. As illustrated, aggrecan coating leads to decreased migration of adult NSCs and ISP treatment alleviates the inhibition of CSPGs on NSCs migration. FIG. 12B graphically illustrates the normalized migration index of the cells under the various conditions illustrated in FIG. 12A. Two way ANOVA,  and * indicate p<0.01 and p<0.001 compared to control treated NSCs and # indicate p<0.05 compared to no aggrecan coated condition. Scale bar=100 um.

FIGS. 13A-13C illustrate that primary PTPσ cKO adult NSCs have increased neurite outgrowth compared to wild type NSCs on aggrecan substrates. FIGS. 13A and 13B are representative images of MAP2 immunostaining in wild type and cKO NSCs, respectively, differentiated in vitro for 5 days. Scale bar=50 um. FIG. 13C graphically illustrates the quantification of neurite length carried out by unbiased imaging and quantification of 50 differentiated neuronal cells. ** indicate p<0.01, Student's t-test.

FIG. 14 is a series of representative images of MAP2 immunostaining in wild type NSCs differentiated in vitro for 5 days. Quantification of neurite length was carried out by unbiased imaging and quantification of 50 differentiated neuronal cells in each condition. FIG. 14 B graphically illustrates neurite length observed for control, cells treated with scrambled peptide, and cells treated with ISP peptide. There is no significant difference between control and scrambled peptide treated cells and ** indicates p<0.01 in ISP-treated cells compared to control or scrambled peptide treated cells. One-way ANOVA.

DETAILED DESCRIPTION

Figure 1:
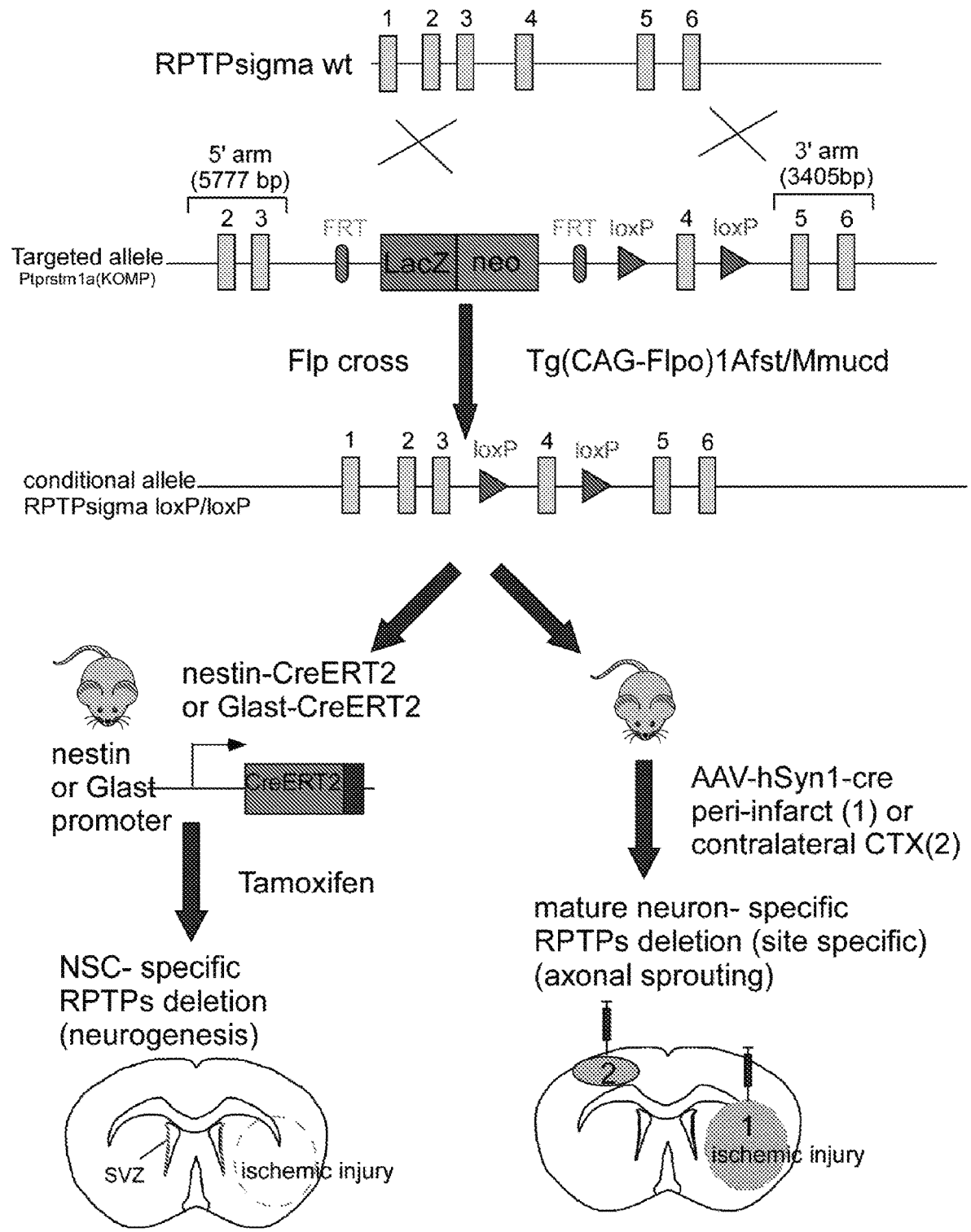
FIG. 1 schematically illustrates an example of an approach to implementing cell-specific deletion of PTPσ in animal models.

This disclosure generally relates to agents, compounds, and methods of treating neural injury, such as neural injury caused by traumatic brain injury (TBI), ischemia, stroke (e.g., ischemic stroke, and/or chronic stroke disease), aneurysm, cerebral hemorrhage, thrombus, embolism, multiple sclerosis (MS), or Alzheimer's disease in a subject in need thereof, as well as to methods for the treatment of diseases or disorders associated with glial scar formation and/or chondroitin sulfate proteoglycan (CSPG) in the nervous system of subjects. In some embodiments, the disclosure relates to promoting compensatory plasticity of spared neural cells after a neural injury.

This disclosure is based, in part, on the inventors' discovery that chondroitin sulfate proteoglycans (CSPGs) can accumulate or regulate in glial scars in peri-infarct regions throughout the chronic stage in both animal and human stroke patients. This accumulation of CSPGs at the peri-infarct region during chronic stage of stroke has been implicated in the inhibition of post-stroke neuronal plasticity reorganization, which includes formation of new local circuits, interhemispheric connections, and corticospinal tract axonal sprouting, potentially causing the limited recovery in stroke animals and human patients. As described in more detail below, the inventors discovered that a systemic peptide treatment (e.g., intracellular sigma peptide (ISP) treatment), which inhibited or modulated PTPσ catalytic activity, signaling, and/or function in neural cells, overcomes the CSPG barrier to remarkably improve multiple aspects of the functional recovery in a murine stroke model, including general locomotor function, specific upper limb sensorimotor function, as well as cognitive function. During investigation of the mechanism of recovery, it was determined that ISP modulation of PTPσ signaling in neural cells contributed to several aspects of recovery by inducing migration and sprouting activity of neural cells spared from the injury (e.g., uninjured neurons) that permitted functionality to compensate for the presence of injured neurons. This ultimately permitted induction of ameliorative effects even when ISP treatment was delayed after the neural injury. Furthermore, the systemic peptide treatment inhibited or modulated PTPσ catalytic activity, signaling, and/or function leading to a decrease in the chronic atrophy of brain after stroke. Thus, this demonstrated ability to promote plasticity of spared (e.g., uninjured) neural cells proximal and distal to the neural injury is highly relevant for therapies to promote recovery and survival after an injury, such as malignant stroke, has occurred.

In accordance with the foregoing, in one aspect the disclosure provides a method of promoting compensatory plasticity of spared neural cells after a neural injury. The method includes contacting the spared neural cells with an effective amount of a therapeutic agent that inhibits or modulates one or more of catalytic activity, signaling, or function of PTPσ in the spared neural cells. This method is applicable to further methods of treatment for neural injury in a subject by promoting compensatory plasticity in spared neural cells after the neural injury by administering an effective amount of the disclosed therapeutic agent or composition to the subject, which are also encompassed by the present disclosure. In some embodiments, the therapeutic agent comprises a therapeutic peptide. The therapeutic peptide can include an amino acid sequence with at least 70% identity to SEQ ID NO: 32 or at least 70% identity to SEQ ID NO: 33.

As used herein, the term "treat" refers to medical management of a disease, disorder, or condition (e.g., neural injury) of a subject (e.g., a human or non-human mammal, such as another primate, horse, dog, pig, mouse, rat, guinea pig, rabbit, and the like). Treatment can encompass any indicia of success in the treatment or amelioration of a disease or condition (e.g., a neural injury), including any parameter such as abatement, remission, diminishing of symptoms or making the disease or condition more tolerable to the patient, slowing in the rate of degeneration or decline, or making the degeneration less debilitating. The treatment or amelioration of symptoms can be based on objective or subjective parameters, including the results of an examination by a physician. For example, the "NIHSS scale" referred to herein is a commonly used scale to measure the level of impairment caused by a stroke (Kasner S E. Lancet Neurol. 2006; 7:603-12). Accordingly, the term "treating" includes the administration of the compositions of the present disclosure to alleviate, or to arrest or inhibit development of the symptoms or conditions associated with disease or condition (e.g., neural injury). In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "therapeutic effect" refers to the general amelioration, reduction, or elimination of the disease or condition, symptoms of the disease or condition, or side effects of the disease or condition in the subject.

The term "therapeutically effective" refers to an amount of the composition that results in a therapeutic effect, such as induced compensatory plasticity in spared neurons and/or increased locomotor function, sensorimotor function, or cognition, which can be readily determined. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

The term "compensatory plasticity" refers to induction of phenotypic changes in healthy neural cells that contribute to neural function that compensates for the loss or degradation neural cells that are injured. The healthy neural cells are referred to as "spared" neural cells, indicating that they were not directly injured in the neural injury addressed by the method.

In some embodiments, the spared neural cells are neural stem cells. Neural stem cells are multi-potent, undifferentiated neural cells that can differentiate ultimately into the neurons and glia of the nervous system. In other embodiments, the spared neural cells can comprise oligodendrocyte progenitor cells (OPCs) and/or glial precursor cells (GPCs). In yet other embodiments, the spared neural cells are neurons. Neurons, or nerve cells, are cells within the nervous tissue that transmit electrical impulses along parts of their bodies (e.g., along axons) to affect communication with other cells via release of neurotransmitters into the small synaptic spaces separating the cells. Neurons, as encompassed by the present disclosure, are distinguishable from neural stem cells by expression of certain cell markers. Specifically, neurons are typically nestin- and DCX+ (for immature neurons) or nestin- and NeuN+ or apt2+ (for mature neurons). Neural stem cells, in contrast, are typically nestin+ and DCX-.

As described in more detail below, it was established that inhibition of the catalytic activity signaling and/or function of PTPσ induced neurite outgrowth in spared neural cells after a neural injury (e.g., stroke). Thus, in some embodiments, the therapeutic agent/peptide induces compensatory neurite outgrowth of the spared neural cells. Neurite outgrowth can manifest in axonal sprouting in the spared neural cells. Axonal sprouting is the extension development, or otherwise growth of an axon, i.e., a nerve fiber, from the cell body. Axons typically function to conduct electrical impulses away from the nerve cell body towards another cell. In other embodiments, the neurite outgrowth can manifest in dendrite sprouting in the spared neural cells. Dendrites are branched protoplasmic extensions of the nerve cell that propagate electrochemical stimulation received from other neural cells to the cell body. In either embodiment, neurite sprouting, whether axonal sprouting or dendrite sprouting or branching, results in increased synaptic contact with neighboring, surrounding, or even distant neural cells. Without being limited to a particular theory, the increased synaptic contacts compensate for the loss synaptic contacts due to injury of other cells. With the increase of compensatory synapses through neurite sprouting, alternative or bypass connections can be established thus rerouting signaling pathways that can serve to recover function after the loss or degradation of an injured neural cell.

In some embodiments, the neurite outgrowth described herein can occur in spared neural cells that are proximal to the site of neural injury, or distal to the site of injury. The terms "proximal" or "distal" are terms that indicate relative distance and can indicate different distances depending on context. In some instances, spared neural cells that are proximal to the site neural injury are cells that are near or otherwise close to the site of injury, e.g. directly contacting an injured neural cell or within a distance measurable in cell lengths or widths from the injured cell. In contrast, spared neural cells that are distal to the site of neural injury can be far away, such as in different tissues or regions of the brain, or even in other regions of the central nervous system, such as in the spinal cord. For example, in some embodiments the therapeutic agent/peptide induces neurite outgrowth in spared neurons that are distal to the site of neural injury, such as in a location in the contralateral corticospinal tract.

In other embodiments, the therapeutic agent/peptide induces compensatory migration of spared neural cells towards the neural injury. In some embodiments, the spared neural cells exhibiting compensatory migration are neural stem cells. In other embodiments, the spared neural cells exhibiting compensatory migration are oligodendrocyte progenitor cells (OPCs) and/or glial precursor cells (GPCs). In some embodiments, the therapeutic agent/peptide induces compensatory migration of spared neural cells that are proximal to the site of neural injury. While the present disclosure encompasses embodiments where compensatory migration of the spared neural cells that result in the spared neural cells entering the site of neural injury, the disclosure is not so limited. The disclosure also encompasses embodiments where compensatory migration of the spared neural cells results in the spared neural cells being closer to the site of neural injury than they were prior to administration of the therapeutic agent/peptide. In some embodiments, the migrating spared neural cells cross a ring of CSPGs.

The disclosed methods address neural injuries that occur in the central nervous system. In some embodiments, the neural injury is in the brain. As described in more detail below, a stroke model was used to establish induced plasticity of spared neural cells after neural injury. Considering that the effect of enhanced plasticity occurred in spared neural cells, including neural cells that are distal to the site of injury, it will be appreciated by a person of ordinary skill in the art that the disclosure is not limited to instances of stroke but also encompasses other forms of neural injury. Accordingly, the neural injury can be caused by traumatic brain injury (TBI), e.g., concussion; neurodegenerative diseases, such as multiple sclerosis (MS); Alzheimer's disease, ischemia (e.g., focal ischemia or global ischemia); stroke (e.g., ischemic stroke, and/or chronic stroke disease); aneurysm, cerebral hemorrhage, thrombus, embolism; and the like where neural cells are damaged.

The term "ischemia", also referred herein as "cerebral ischemia," "brain ischemia," or "cerebrovascular ischemia", is a condition in which there is insufficient blood flow to the brain to meet metabolic demand. This leads to poor oxygen supply or cerebral hypoxia and thus to the death of brain tissue or cerebral infarction also referred as "ischemic stroke". "Ischemic stroke" is a sub-type of stroke and is typically the result of the interruption of blood supply to the brain due to an occlusion of a cerebral artery. The terms "cerebral ischemia" and "ischemic stroke" can be used interchangeably herein.

There are two types of cerebral ischemia: "focal ischemia", which is confined to a specific region of the brain; and "global ischemia", which encompasses wide areas of brain tissue. Typically, cerebral ischemia is characterized by the patient presenting one or more of the following symptoms: trouble with speaking and understanding, paralysis or numbness of the face, arm or leg, trouble with seeing in one or both eyes, headache and trouble with walking. To determine the type of stroke and the most appropriate treatment, the emergency team needs to evaluate the type of stroke and the areas of the brain affected by the stroke. They also need to rule out other possible causes of the symptoms, such as a brain tumor or a drug reaction. There are several tests that are generally used to determine the type of stroke: physical examination, blood tests (glucose levels, counting of blood cells, serum electrolytes such as sodium, potassium or calcium, cholesterol, total lipids, HDL, LDL or coagulation factors such as antithrombin III, protein C, protein S; factor VIII; activated Protein C resistance; specially relevant are coagulation factors and platelets determination), computerized tomography (CT) scan, magnetic resonance imaging (MRI), carotid ultrasound, cerebral angiogram and echocardiogram. For a review on diagnosis of ischemic stroke, see Am Fam Physician., 2015, 91(8):528-36. The acute phase of ischemic stroke is referred herein as "acute ischemic stroke" and defined as within 4 hours of onset. The chronic phase of stroke or ischemic stroke is referred herein as chronic stroke disease and occurs after the acute phase of ischemic stroke.

The inhibition of one or more of catalytic activity, signaling, or function of PTPσ in the spared neural cells and therapeutic agents for this purpose will now be described.

The activity, signaling, and/or function of PTPσ can be suppressed, inhibited, and/or blocked in several ways including: direct inhibition of the activity of the intracellular domain of the PTPσ (e.g., by using small molecules, peptidomimetics, antibodies, intrabodies, or dominant negative polypeptides); activation of genes and/or proteins that inhibit one or more of, the activity, signaling, and/or function of the intracellular domain of PTPσ (e.g., by increasing the expression or activity of the genes and/or proteins); inhibition of genes and/or proteins that are downstream mediators of the PTPσ (e.g., by blocking the expression and/or activity of the mediator genes and/or proteins); introduction of genes and/or proteins that negatively regulate one or more of, activity, signaling, and/or function of PTPσ (e.g., by using recombinant gene expression vectors, recombinant viral vectors or recombinant polypeptides); or gene replacement with, for instance, a hypomorphic mutant of PTP (e.g., by homologous recombination, overexpression using recombinant gene expression or viral vectors, or mutagenesis).

The therapeutic agent that inhibits or reduces one or more of the activity, signaling, and/or function of PTPσ can include an agent that decreases and/or suppresses the activity, signaling, and/or function of PTPσ. Such agents can be delivered intracellularly and once delivered intracellularly enhance at least one of locomotor function, sensorimotor function, or cognition in the subject.

In some embodiments, the therapeutic agent that inhibits or reduces one or more of the activity, signaling, and/or function of PTPσ, comprises a therapeutic peptide or small molecule that binds to and/or complexes with the intracellular domain of PTPσ, in particular, the intracellular wedge shaped domain, to inhibit the activity, signaling, and/or function of PTPσ. Accordingly, therapeutic peptides or small molecules that bind to and/or complex with the intracellular domain of PTPσ of spared neural cells (e.g. neural stem cells, OPC's, GPC's, neurons, and/or glial cells) can be used to promote compensatory cell growth, motility (e.g. migration), neurite outgrowth, survival or other characteristics promoting compensatory plasticity of these cells.

In some embodiments, the therapeutic agent can be a peptide mimetic of the wedge shaped domain (i.e., wedge domain) of the intracellular catalytic domain of PTPσ, such as described, for example, in WO 2013/155103A1, which is herein incorporated by reference in its entirety. Peptide mimetics of the wedge domain of the PTPσ when expressed in cells (e.g., neurons and/or glial cells) or conjugated to an intracellular transport moiety can bind to and/or cameras with the wedge domain expressed in the spared neural cell resulting in abolishment of PTPσ signaling in the spared neural cells to promote cell growth, motility, and survival. For example, binding of these therapeutic peptides to PTPσ intact wedge domain can: (i) interfere with the ability for PTPσ to interact with target proteins, such as phosphatase targets; (ii) interfere with activity promoting intermolecular interactions between PTPσ and another domain contained in PTPσ, such as the catalytically inactive second phosphatase domain D2; (iii) prevent access of proteins to the active phosphatase site; (iv) out-compete normal interactors of the wedge domain; and/or (v) sterically inhibit phosphatase activity.

As indicated above, in some embodiments the therapeutic agent can comprise, consist essentially, and/or consist of a therapeutic peptide that comprises an amino acid sequence of about 10 to about 20 amino acids that has at least about 70%, at least about 75%, at least about 80%, at least about 85%, at least about 90%, at least about 95%, or 100% identical to an about 10 to about 20 consecutive amino acid portion of the amino acid sequence of the wedge domain of PTPσ. In some embodiments, the about 10 to about 20 consecutive amino acid portion includes consecutive amino acids of N-terminal alpha helix and 4 amino acid turn of the wedge domain. In some embodiments, the reference wedge domain of PTPσ is a human PTPσ sequence. In some embodiments, the therapeutic peptide comprises an amino acid sequence with at least about 70%, at least about 78%, at least about 85%, at least about 92%, or 100% identity to SEQ ID NO: 32. In other embodiments, the therapeutic peptide comprises an amino acid sequence with at least about 70%, at least about 78%, at least about 85%, at least about 92%, or 100% identity to SEQ ID NO: 33.

As disclosed below, a peptide (e.g., therapeutic peptide) corresponding to or substantially identical to the wedge domain of PTPσ with a cytosolic-carrier was able to relieve CSPG-mediated inhibition of post-stroke neuronal plasticity reorganization enhance at least one of locomotor function, sensorimotor function, or cognition. Advantageously, the therapeutic peptide can be administered systemically.

As shown in Table 1, the wedge domain sequence of PTPσ is highly conserved among higher mammals, with only a single amino acid change in humans to mouse and rats (Threonine to Methionine at position 6) preventing 100% homology.

TABLE 1

Alignment of wedge domain protein sequences.

| Residue/position | | | | | | | | | | | | | | | | | | | | | | | | Source organism | SEQ ID NO |
|---|---|---|---|---|---|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | | |
| D | L | A | E | H | T | E | H | L | K | A | N | D | N | L | K | | S | Q | E | Y | E | S | | Xenopus | 1 |
| D | H | T | E | H | | | | L | K | A | N | D | N | L | K | L | S | Q | E | Y | E | S | I | Green anole | 2 |
| E | L | A | E | H | T | E | L | L | K | A | N | D | N | L | K | L | S | Q | E | Y | E | S | I | Zebrafish | 3 |
| E | L | A | E | H | T | E | L | L | K | A | N | D | N | L | K | L | S | Q | E | Y | E | S | I | Talapia | 4 |

TABLE 1-continued

Alignment of wedge domain protein sequences.

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | Source organism | SEQ ID NO |
|---|---|---|---|---|---|---|---|---|----|----|----|----|----|----|----|----|----|----|----|----|----|----|----|---|---|
| E | L | A | E | H | T | E | H | L | K | A | N | D | N | L | K | L | S | Q | E | Y | E | S | I | Chicken | 5 |
| E | L | A | E | H | T | E | H | L | K | A | N | D | N | L | K | L | S | Q | E | Y | E | S | I | Finch | 6 |
| E | L | A | E | H | T | D | H | L | K | A | N | D | N | L | K | L | S | Q | E | Y | E | S | I | Platypus | 7 |
| E | M | A | E | H | T | E | H | L | K | A | N | D | N | L | K | L | S | Q | E | Y | E | S | I | Tazmanian Devil | 8 |
| D | M | A | E | H | T | E | R | L | K | A | N | D | S | L | K | L | S | Q | E | Y | E | S | I | Ferret | 9 |
| D | M | A | E | H | T | E | R | L | K | A | N | D | S | L | K | L | S | Q | E | Y | E | S | I | Bush-Baby | 10 |
| D | M | A | E | H | T | E | R | L | K | A | N | D | S | L | K | L | S | Q | E | Y | E | S | I | Marmoset | 11 |
| D | M | A | E | H | T | E | R | L | K | A | N | D | S | L | K | L | S | Q | E | Y | E | S | I | RAT | 12 |
| D | M | A | E | H | M | E | R | L | K | A | N | D | S | L | K | L | S | Q | E | Y | E | S | I | Mouse | 13 |
| D | M | A | E | H | T | E | R | L | K | A | N | D | S | L | K | L | S | Q | E | Y | E | S | I | Dog | 14 |
| D | M | A | E | H | T | E | R | L | K | A | N | D | S | L | K | L | S | Q | E | Y | E | S | I | Pig | 15 |
| D | M | A | E | H | T | E | R | L | K | A | N | D | S | L | K | L | S | Q | E | Y | E | S | I | Cow | 16 |
| D | M | A | E | H | T | E | R | L | K | A | N | D | S | L | K | L | S | Q | E | Y | E | S | I | Sheep | 17 |
| D | M | A | E | H | T | E | R | L | K | A | N | D | S | L | K | L | S | Q | E | Y | E | S | I | Killer Whale | 18 |
| D | M | A | E | H | T | E | R | L | K | A | N | D | S | L | K | L | S | Q | E | Y | E | S | I | Squirrel Monkey | 19 |
| D | M | A | E | H | T | E | R | L | K | A | N | D | S | L | K | L | S | Q | E | Y | E | S | I | Baboon | 20 |
| D | M | A | E | H | T | E | R | L | K | A | N | D | S | L | K | L | S | Q | E | Y | E | S | I | Gorilla | 21 |
| D | M | A | E | H | T | E | R | L | K | A | N | D | S | L | K | L | S | Q | E | Y | E | S | I | Gibbon | 22 |
| D | M | A | E | H | T | E | R | L | K | A | N | D | S | L | K | L | S | Q | E | Y | E | S | I | Macaque | 23 |
| D | M | A | E | H | T | E | R | L | K | A | N | D | S | L | K | L | S | Q | E | Y | E | S | I | Chimpanzee | 24 |
| D | M | A | E | H | T | E | R | L | K | A | N | D | S | L | K | L | S | Q | E | Y | E | S | I | Human | 25 |
| D | L | A | D | N | I | E | R | L | K | A | N | D | G | L | K | F | S | Q | E | Y | E | S | I | LAR (Lar family) | 26 |
| E | L | A | D | H | I | E | R | L | K | A | N | D | N | L | K | F | S | Q | E | Y | E | S | I | Delta (Lar family) | 27 |
| K | L | E | E | E | I | N | R | R | M | A | D | D | N | K | I | F | R | E | E | F | N | A | L | ptp alpha | 28 |

As shown in Table 1, the first alpha helix of the wedge domain of PTP includes amino acids 1-10, the turn region includes amino acids 11-14, and the second alpha helix includes amino acids 15-24. For example, the first alpha helix of the wedge domain of human PTPσ (SEQ ID NO: 25) has the amino acid sequence of DMAEHTERLK (SEQ ID NO: 29), the turn has the amino acid sequence of ANDS (SEQ ID NO: 30), and the second alpha helix has the amino acid sequence of LKLSQEYESI (SEQ ID NO: 31).

The wedge domain also shares sequence homology with the other members of the LAR family, LAR and PTPδ. It is likely that these amino acids are necessary for the overall structure of the wedge domain. Conserved amino acids include an alanine at position 13, which marks the end of the first alpha helix and the start of the turn, making it likely to be necessary for general wedge size and structure.

Because the general secondary and tertiary structures of the wedge domain remain consistent through most receptor PTPs, several conservative substitutions can be made to a therapeutic peptide targeting the PTPσ wedge domain to obtain similar results. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, and/or the substitution of one acidic residue, such as aspartic acid or glutamic acid for another.

These conservative substitutions can occur in the non-unique domains in either alpha helix or the turn, specifically positions 1-3 and 7-10 in the first alpha helix; 12 and 13 in the turn; and 15, 16, 18-24 in the second alpha helix. These amino acids may be necessary to the overall structure of the wedge domain, but not necessary for specificity of binding of wedge to PTPσ.

The unique amino acids to PTPσ, particularly the amino acids expressed differentially in PTPσ vs LAR, were found to be necessary for specificity of wedge domain binding. These include an EH domain in the first alpha helix position 4 and 5 followed by a threonine or a methionine (rat and mouse substitution) at position 6. In the turn, there is a unique serine at position 14 in all higher mammals. Finally, there is a unique leucine at position 17 in the second alpha helix. The potential roles of these unique amino acids will be discussed below.

The serine residue in the turn at position 14 is of particular interest due to its location in the wedge domain. This amino acid, located in the turn between alpha helixes, is slightly extended from the general secondary and tertiary structure of PTPσ, making it available for binding interactions. In addition, serine, due to its hydroxyl group and the polarity it contains, is known to facilitate several homophillic and heterophillic binding events, such as hydrogen binding between adjacent serines. Serines are also known to undergo various modifications, such as phosphorylation, making the likelihood of its necessity for specificity high. It is possible that smaller peptides that focus on the turn in the wedge domain and include the conserved serine may offer greater stability with similar function. Such peptides can be synthesized as loops, with cysteines on either end to created di-sulfide bonds.

The unique amino acids in the first alpha helix include glutamic acid at position 4, histidine at position 5 and threonine or methionine at position 6. Although the histidine is implicated in the consensus wedge domain, it is not found in LAR, PTPδ, PTPμ or CD45. As all three of these amino acids are either charged or polar, it is likely that either this sequence or one of its components is necessary for PTPσ wedge specificity.

Additionally, the second alpha helix contains a unique leucine at position 17. Leucines have been implicated as the critical adhesive molecules for the three dimensional structure of leucine zippers. In these molecules, which are structurally similar to wedge domains, leucines of opposing alpha helixes, located at approximately 7 intervals, interact with hydrophobic regions of the opposing alpha helix. As there is also a Leucine in the first alpha helix, located at position 9, it is believed that this unique leucine is necessary for the overall three-dimensional structural integrity of the PTPσ wedge.

Accordingly, in some embodiments the therapeutic peptide can comprise, consist essentially of, or consist of about 14 to about 20 amino acids and include the amino acid sequence EHX1ERLKANDSLKL (SEQ ID NO: 32), wherein $X_1$ is T or M. A therapeutic peptide including SEQ ID NO: 32 can include at least one, at least two, at least three, at least four, or at least five conservative substitutions so that the therapeutic peptide has an amino acid sequence that is at least about 70%, at least about 78%, at least about 85%, at least about 92%, or 100% identical to SEQ ID NO: 32.

In some embodiments, the conservative substitutions can be of amino acid residues 4E, 5R, 6L, 7K, 9N, 10D, 12L, or 13K of SEQ ID NO: 32. By way of a nonlimiting example, amino acid residue 4E can be substituted with D or Q, amino acid residue 5R can be substituted with H, L, or K, amino acid residue 6L can be substituted with I, V, or M, amino acid residue 7K can be substituted with R or H, amino acid residue 9N can be substituted with E or D, amino acid residue 10 D can be substituted with E or N, amino acid residue 12L can be substituted with I, V, or M, and/or amino acid residue 13K can be substituted with R or H. Any one or more of the indicated substitutions can be implemented in any combination so long as the resulting sequence achieves the identity parameters described above.

Many aspects of the description of the therapeutic peptide are generally presented herein in the context of SEQ ID NO: 32, the disclosure also encompasses embodiments where the therapeutic peptide comprises a variant in the wedge domain as set forth in SEQ ID NO: 33. It will be understood that all other facets and characteristics of the therapeutic peptide described herein also apply to this variant embodiment, unless specifically stated otherwise. Thus, in other embodiments the therapeutic peptide can include, consist essentially of, or consist of about 14 to about 20 amino acids and include the amino acid sequence DMAEHX$_1$ERLKANDS (SEQ ID NO: 33), wherein $X_1$ is T or M. A therapeutic peptide including SEQ ID NO: 33 can include at least one, at least two, at least three, at least four, or at least five conservative substitutions so that the therapeutic peptide has an amino acid sequence that is at least about 65%, at least about 70%, at least about 75%, at least about 80%, at least about 85%, at least about 90%, or at least about 95% identical to SEQ ID NO: 33.

In some embodiments, the conservative substitutions can be of amino acid residues 7E, 8R, 9L, 10K, 12N, or 13D of SEQ ID NO: 33. By way of example, amino acid residue 7E can be substituted with D or Q, amino acid residue 8R can be substituted with H, L, or K, amino acid residue 9L can be substituted with I, V, or M, amino acid residue 10K can be substituted with R or H, amino acid residue 12N can be substituted with E or D, and amino acid residue 13 D can be substituted with E or N.

In some embodiments, the therapeutic peptide comprises an amino acid sequence selected from the group consisting of SEQ ID NOs: 1-25, 32 and 33.

The therapeutic peptides described herein can be subject to other various changes, substitutions, insertions, and deletions where such changes provide for certain advantages in its use. In this regard, therapeutic peptides that bind to and/or complex with a wedge domain of PTPσ can correspond to or have substantial but incomplete identity to the sequence of a recited polypeptide where one or more changes are made and it retains the ability to inhibit or reduce one or more of the activity, signaling, and/or function of PTP function.

The therapeutic peptide can be in any of a variety of forms of polypeptide derivatives that include amides, conjugates with proteins, cyclized polypeptides, polymerized polypeptides, analogs, fragments, chemically modified polypeptides and the like derivatives.

It will be appreciated that the conservative substitution can also include the use of a chemically derivatized residue in place of a non-derivatized residue provided that such peptide displays the requisite binding activity.

As used herein the term "chemical derivative," or grammatical variations thereof, refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein may also include any polypeptide having one or more additions and/or deletions or residues relative to the sequence of a polypeptide whose sequence is shown herein, so long as the requisite activity is maintained.

One or more of peptides of the therapeutic peptides described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise, for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may function as inhibitors of the LAR family phosphatases (without being restricted to the present examples).

The therapeutic polypeptides described herein may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the polypeptides may be done by affinity methods, ion exchange chromatography, size exclusion chromatography, hydrophobicity or other purification technique typically used for protein purification. The purification step can be performed under non-denaturating conditions. On the other hand, if a denaturating step is required, the protein may be renatured using techniques known in the art.

In some embodiments, the therapeutic peptides described herein can include additional residues that may be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half-life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 1, 2, 3, 4, 5, 6, 7, 8, 9, 10, 11, and 12. In some cases, a peptide linker comprises two or more of the following amino acids: glycine, serine, alanine, and threonine, in any combination. In some embodiments, the peptide linker does not contain a cysteine residue.

In some embodiments, a therapeutic agent comprising the therapeutic peptides described herein can be provided in the form of a conjugate protein or drug delivery construct includes at least a transport subdomain(s) or moiety(ies) (i.e., transport moieties) that is linked to the therapeutic peptide. The transport moieties can facilitate uptake of the therapeutic polypeptides into a mammalian (i.e., human or animal) tissue or cell (e.g., neural cell). The transport moieties can be covalently linked to the therapeutic peptides. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the therapeutic polypeptide. The transport moieties can also be linked to the therapeutic polypeptide with linking polypeptide described herein.

The transport moieties can be repeated more than once in the therapeutic agent. The repetition of a transport moiety may affect (e.g., increase) the uptake of the peptides and/or proteins by a desired cell. The transport moiety may also be located either at the amino-terminal region of therapeutic peptide or at its carboxy-terminal region or at both regions.

In some embodiments, the transport moiety can include at least one transport peptide sequence that allows the therapeutic polypeptide once linked to the transport moiety to penetrate into the cell by a receptor-independent mechanism. An example of a Tat sequence encompassed by the present disclosure is set forth in SEQ ID NO: 34. For example, in illustrative, nonlimiting embodiments the transport peptide is a synthetic fusion peptide that contains at least a Tat-mediated protein delivery sequence and sequence at least 70% identical to one of SEQ ID NOs: 1-25, 32, and 33. In specific illustrative embodiments, where the Tat-mediated protein delivery sequence is linked to the wedge domain sequence of one of SEQ ID NOs:1-25, 32, and 33 with a peptide linker of one residue, the fusion peptides can have, respectively, the amino acid sequences of SEQ ID NOs:35-61. The Xaa indicated for each of SEQ ID NOs: 35-59 (and the first Xaa indicated for each of SEQ ID NOs: 60 and 61), can be any amino acid residue, such as glycine, tyrosine, cysteine, lysine, glutamic and aspartic acid, or the like. In some embodiments, the indicated linker amino acid (indicated with Xaa) is a glycine, serine, alanine, or threonine. In some embodiments, the indicated linker amino acid (indicated with Xaa) is not cysteine. While SEQ ID NOs: 35-61 disclose sequences each with a single linker amino acid residue, it will be understood that other embodiments with longer peptide linkers comprising two or more amino acid residues are also encompassed by this disclosure. Longer peptide linkers are described above.

Other examples of known transport moieties, subdomains, and the like, encompassed by the present disclosure, are described in, for example, Canadian patent document No. 2,301,157 (conjugates containing homeodomain of antennapedia) as well as in U.S. Pat. Nos. 5,652,122, 5,670, 617, 5,674,980, 5,747,641, and 5,804,604, all of which are incorporated herein by reference in their entireties. Such examples include conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No. 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example, 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the therapeutic peptide described herein can be non-covalently linked to a transduction agent. An example of a non-covalently linked polypeptide transduction agent is the Chariot protein delivery system (see U.S. Pat. No. 6,841,535; *J Biol Chem* 274(35):24941-24946; and *Nature Biotec.* 19:1173-1176, all herein incorporated by reference in their entireties).

The therapeutic agents described herein can be modified (e.g., chemically modified). Such modification can be designed to facilitate manipulation or purification of the molecule, to increase solubility of the molecule, to facilitate administration, targeting to the desired location, to increase or decrease half-life. A number of such modifications are known in the art and can be applied by the skilled practitioner.

In an embodiment, methods of treatment disclosed herein, a therapeutically effective amount of the therapeutic agent is administered to a subject with chronic functions associated with chronic stroke disease. A formulation including the therapeutic agent can be administered one or more times to the subject in the period from the time of, for example, detection or onset of the stroke, to days, weeks, months, and/or years after the detection or onset of the stroke.

The therapeutic agents can be delivered to a subject by any suitable route, including, for example, local and/or systemic administration. Systemic administration can include, for example, parenteral administration. The phrase "parenteral administration" refers to modes of administration other than enteral and topical administration, typified by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion. In some embodiments, the systemic administration includes intramuscular, intravenous, intraarticular, intraarterial, intrathecal, intravitreal, subcutaneous, or intraperitoneal administration. The agent can also be administered orally, transdermally, topically, by inhalation (e.g., intrabronchial, intranasal, oral inhalation or intranasal drops) or rectally. In some embodiments, the therapeutic agent can be administered to the subject via intravenous administration using an infusion pump to deliver daily or weekly, doses of the therapeutic agent.

Desirable features of local administration can include achieving effective local concentrations of the therapeutic agent, as well as avoiding potential adverse side effects from systemic administration of the therapeutic agent. In one embodiment, the therapeutic agent can be introduced directly into the brain of the subject.

Pharmaceutically acceptable formulations of the therapeutic agent can be suspended in aqueous vehicles and introduced through conventional hypodermic needles or using infusion pumps.

For injection, therapeutic agent can be formulated in liquid solutions, typically in physiologically compatible buffers such as Hank's solution or Ringer's solution. In addition, the therapeutic agent may be formulated in solid form and re-dissolved or suspended immediately prior to use. Lyophilized forms are also provided. The injection can be, for example, in the form of a bolus injection or continuous infusion (such as using infusion pumps) of the therapeutic agent.

It will be appreciated that the amount, volume, concentration, and/or dosage of the therapeutic agent that is administered to any animal or human subject depends on many factors, including the subject's size, body surface area, age, the particular composition to be administered, sex, time and route of administration, general health, and other drugs being administered concurrently. Specific variations of the above noted amounts, volumes, concentrations, and/or dosages of therapeutic agent can be readily determined by one skilled in the art using the experimental methods described below.

In some embodiments, a therapeutic agent, such as a therapeutic peptide described herein, can be administered locally and/or systemically to a subject in need thereof at a dose or amount of about 0.1 µmol, about 1 µmol, about 5 µmol, about 10 µmol, or more; or about 0.0001 mg/kg, about 0.001 mg/kg, about 0.01 mg/kg, about 0.1 mg/kg, or about 1 mg/kg to about 5 mg/kg or 10 mg/kg of the subject being treated. The therapeutic agent can be administered daily, weekly, biweekly, monthly or less frequently until there is maximal recovery of locomotor, sensorimotor, and/or cognitive deficits.

The therapeutic agent can be administered at a fixed unit dose of between 1-1000 mg IV, e.g., between 100-600 mg IV, e.g., between 200 and 400 mg IV, e.g., about 300 mg IV. When administered subcutaneously, the therapeutic agent is typically administered at a dose between 1 mg-100 mg SC (e.g., 75 mg). It can also be administered in a bolus at a dose of between 1 and 10 mg/kg, e.g., about 6.0, 4.0, 3.0, 2.0, 1.0 mg/kg. In some cases, continuous administration may be indicated, e.g., via a subcutaneous pump.

In some embodiments the spared neural cells are contacted with the therapeutic agent within 7 days post injury, e.g. within about 1, about 2, about 3, about 4, about 5, about 6, and about 7 days after the neural injury occurs.

In embodiments of treatment of a subject, the subject is administered the therapeutic agent within 7 days post injury, e.g. within about 1, about 2, about 3, about 4, about 5, about 6, and about 7 days after the neural injury occurs. For example, in some embodiments, the therapeutic agent, e.g., the therapeutic peptide, is administered to a subject after 12 hours or more, e.g., 13, 14, 15, 16, 17, 18, 19, 10, 21, 22, 23, or 24 hours or more after the onset of a neural injury such as a stroke. For example, the therapeutic agent can be administered after acute stroke or after about 12 hours or more from onset of stroke.

In another embodiment, the therapeutic agent can be administered to a subject systemically by intravenous injection or locally at the site of injury, usually after about 24 hours, about 48 hours, about 100 hours, or about 200 hours or more of when a neural injury, e.g., a stroke, occurs.

In other embodiments, a pharmaceutically acceptable formulation used to administer the therapeutic agent(s) can also be formulated to provide sustained delivery of the active compound to a subject. For example, the formulation may deliver the active compound for at least one, two, three, or four weeks, inclusive, following initial administration to the subject. For example, a subject to be treated in accordance with the method described herein can be treated with the therapeutic agent for at least 30 days (either by repeated administration or by use of a sustained delivery system, or both).

Approaches for sustained delivery include use of a polymeric capsule, a minipump to deliver the formulation, a biodegradable implant, or implanted transgenic autologous cells (see U.S. Pat. No. 6,214,622). Implantable infusion pump systems (e.g., INFUSAID pumps (Towanda, PA)); see Zierski et al., 1988; Kanoff, 1994) and osmotic pumps (sold by Alza Corporation) are available commercially and otherwise known in the art. Another mode of administration is via an implantable, externally programmable infusion pump. Infusion pump systems and reservoir systems are also described in, e.g., U.S. Pat. Nos. 5,368,562 and 4,731,058.

The pharmaceutical compositions can be administered to any subject that can experience the beneficial effects of compensatory neural plasticity, for example plasticity manifesting in enhanced locomotor function, sensorimotor function, and/or cognition. Foremost among such animals are humans, although embodiments described herein are not intended to be so limited.

As indicated, the described therapeutic agent can be used in a method of treating neural injury in the subject. The method can include administering to the subject in need thereof a therapeutically effective amount of therapeutic agent described herein. The therapeutically effective amount can include an amount (dose) effective in enhancing compensatory plasticity of spared neural cells, for example plasticity that can manifest in at least one of locomotor function, sensorimotor function, or cognition in the subject.

In some embodiments, the therapeutic agent described herein can be administered in an amount effective to enhance generation of neural cells, e.g., NSCs, neurons, and/or glial cells, in the subject's central nervous system by an increase in the amount of neurons and/or glial cells generation of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the amount of neural cells, e.g., NSCs, neurons, and/or glial cells, in the subject without administration of the therapeutic agent.

In some embodiments, a subject treated by the methods described herein has suffered from an acute middle cerebral artery (MCA) ischemic event or stroke, e.g., ischemic stroke. Ischemic stroke is the rapidly developing loss of brain function(s) due to disturbance in the blood supply to the brain due to ischemia (lack of glucose and oxygen supply) caused by thrombosis (e.g., venous thrombosis), embolism, or systemic hypoperfusion. As a result, the affected area of the brain is unable to function, leading to inability to move one or more limbs on one side of the body, inability to understand or formulate speech, or inability to see one side of the visual field.

Symptoms of acute middle cerebral artery (MCA) ischemic event or ischemic stroke include, e.g., hemiplegia, decreased sensation and muscle weakness of the face, numbness, reduction in sensory or vibratory sensation, altered smell, taste, hearing or vision (total or partial), drooping of eyelid (ptosis) and weakness of ocular muscles, decreased reflexes, balance problems and nystagmus, altered breathing and heart rate, weakness in sternocleidomastoid muscle with inability to turn head to one side, weakness in tongue (inability to protrude and/or move from side to side), aphasia, apraxia, visual field defect, memory deficits, hemineglect, disorganized thinking, confusion, hypersexual gestures, anosognosia, trouble walking, altered movement coordination, and vertigo and/or disequilibrium.

Ischemic event or stroke, e.g., ischemic stroke, onset time may be determined by any available method. For example, a subject may be questioned, e.g., by a physician, regarding various symptoms of stroke, e.g., as described herein, to identify the approximate time of stroke onset. In some cases, stroke onset time is difficult to pinpoint, such as when a subject awakens with stroke, or if the start of symptoms are otherwise undetectable. In such cases, stroke onset may be determined by identifying the time the subject was last known to be well, e.g., last known normal (LKN). In some cases, MRI of the brain can be used to determine onset time and/or stroke duration in a subject (see, e.g., Petkova et al.; Radiology (2010) MR imaging helps predict time from symptom onset in patients with acute stroke: implications for patients with unknown onset time, 257(3):782-92, incorporated herein by reference in its entirety).

In some embodiments, the method of treating a neural injury in a subject in need thereof, as described herein, further comprises administering an additional therapy for the neural injury. Stated otherwise, the presently disclosed method of treating can be part of a combination therapy in addressing neural injury. For example, additional therapies for treating stroke can also include, e.g., thrombolysis (e.g., tissue plasminogen activator (tPA)), thrombectomy, angioplasty and stenting, therapeutic hypothermia, and medications (e.g., aspirin, clopidogrel and dipyridamole). In some embodiments, the additional therapy is, e.g., a thrombolytic agent, a neuroprotective agent, an anti-inflammatory agent, a steroid, a cytokine or a growth factor. The thrombolytic agent used can be tissue plasminogen activator or urokinase. The neuroprotective agent used can be an agonist to a receptor selected from the group consisting of: N-Methyl-D aspartate receptor (NMDA), a-amino-3-hydroxy-5-methyl-4-isoxazoleproprionic acid receptor (AMPA), glycine receptor, calcium channel receptor, bradykinin B2 receptor and sodium channel receptor, or from the group consisting of: the bradykinin B1 receptor, α-amino butyric acid (GABA) receptor, and Adenosine A1 receptor. Anti-inflammatory agents for use can be interleukin-1 and tumor necrosis factor family members.

Standard tests for neurological recovery (e.g., National Institute of Health Stroke Scale (NIHSS), Barthel Index, modified Rankin Scale (mRS), Glasgow Outcome Scale, Montreal Cognative Assessment (MoCA), Stroke Impact Scale (SIS-16)) can be employed by skilled artisans to determine efficacy. The NIHSS classifies the severity of a stroke based on a subject's ability to answer questions and perform activities relating to level of consciousness, language, visual-field loss, extraocular movement, motor strength, ataxia, dysarthria, sensory loss and extinction and inattention. There are 15 items and ratings for each item are scored with 3 to 5 grades with 0 as normal and a maximum severity score of 42 for all items. A NIHSS of 1-4 is indicative of a minor stroke; a score of 5-15 is indicative of a moderate stroke, a score of 16-20 is indicative of a moderate to severe stroke; and a score of 21-42 is indicative of a severe stroke.

General Definitions

Unless specifically defined herein, scientific and technical terms used herein shall have the meanings that are commonly understood by those of ordinary skill in the art. Practitioners are particularly directed to Ausubel, F. M., et al. (eds.), *Current Protocols in Molecular Biology*, John Wiley & Sons, New York (2010); Coligan, J. E., et al. (eds.), *Current Protocols in Immunology*, John Wiley & Sons, New York (2010); Mirzaei, H. and Carrasco, M. (eds.), *Modern Proteomics-Sample Preparation, Analysis and Practical Applications in Advances in Experimental Medicine and Biology*, Springer International Publishing, (2016); Comai, L, et al., (eds.), *Proteomic: Methods and Protocols in Methods in Molecular Biology*, Springer International Publishing, (2017); Alberts, B., et al. Molecular Biology of the Cell, W. W. Norton & Company; Sixth edition (2014); and Kandel, E. R., et al. *Principles of Neural Science*, McGraw-Hill Education/Medical; 5th edition (2012) for definitions and terms of art.

For convenience, certain terms employed herein, in the specification, examples and claims are provided here. The definitions are provided to aid in describing particular embodiments and are not intended to limit the claimed invention, because the scope of the invention is limited only by the claims.

Unless otherwise required by context, singular terms shall include pluralities and plural terms shall include the singular. The words "a" and "an," when used in conjunction with the word "comprising" in the claims or specification, denotes one or more, unless specifically noted. The use of the term "or" in the claims is used to mean "and/or" unless explicitly indicated to refer to alternatives only or the alternatives are mutually exclusive, although the disclosure supports a definition that refers to only alternatives and "and/or."

Unless the context clearly requires otherwise, throughout the description and the claims, the words "comprise," "comprising," and the like, are to be construed in an inclusive sense as opposed to an exclusive or exhaustive sense, which is to indicate, in the sense of "including, but not limited to." Words using the singular or plural number also include the plural and singular number, respectively. The term "consist (s) essentially or indicates that the reference composition can include additional elements, variations, and/or sequence, but which additional elements, variations, and/or sequence do not contribute significantly to the functionality of" the indicated composition.

The word "about" indicates a number within range of minor variation above or below the stated reference number indicating, e.g., a quantity, level, value, number, frequency, percentage, dimension, size, amount, weight, or length. For example, "about" can refer to a number within a range of 10%, 9%, 8%, 7%, 6%, 5%, 4%, 3%, 2%, or 1% above or below the indicated reference number.

As used herein, the terms "polypeptide" or "protein" refers to a polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein also encompass any amino acid sequence and includes modified sequences such as glycoproteins. The term polypeptide is specifically intended to cover naturally occurring proteins, as well as those that are recombinantly or synthetically produced. The term "peptide" simply refers to a relatively short polypeptide polymer, for example, up to about 20, about 30, about 40, about 50, about 60, about 70, about 80, or about 90 amino acids in length. The terms "chimeric" or "fusion" in the context of a protein or peptide refer to a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

One of skill will recognize that individual substitutions, deletions or additions to a peptide, polypeptide, or protein sequence which alters, adds or deletes a single amino acid or a percentage of amino acids in the sequence is a "conservatively modified variant" where the alteration results in the substitution of an amino acid with a chemically similar amino acid. Conservative amino acid substitution tables providing functionally similar amino acids are well known to one of ordinary skill in the art. The following six groups are examples of amino acids that are considered to be conservative substitutions for one another:

(1) Alanine (A), Serine (S), Threonine (T),
(2) Aspartic acid (D), Glutamic acid (E),
(3) Asparagine (N), Glutamine (Q),
(4) Arginine (R), Lysine (K),
(5) Isoleucine (I), Leucine (L), Methionine (M), Valine (V), and
(6) Phenylalanine (F), Tyrosine (Y), Tryptophan (W).

Reference to sequence identity addresses the degree of similarity of two polymeric sequences, such as protein sequences. Determination of sequence identity can be readily accomplished by persons of ordinary skill in the art using accepted algorithms and/or techniques. Sequence identity is typically determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. Various software driven algorithms are readily available, such as BLAST N or BLAST P to perform such comparisons.

The term "wild type" (or "wt") refers to the naturally-occurring polynucleotide sequence encoding a protein, or a portion thereof, or protein sequence, or portion thereof, respectively, as it normally exists in vivo.

The agents, compounds, compositions, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence.

The terms "portion", "fragment", "variant", "derivative" and "analog", when referring to a polypeptide include any polypeptide that retains at least some biological activity referred to herein (e.g., inhibition of an interaction such as binding). Polypeptides as described herein may include portion, fragment, variant, or derivative molecules without limitation, as long as the polypeptide still serves its function. Polypeptides or portions thereof of the present invention may include proteolytic fragments, deletion fragments and in particular, or fragments that more easily reach the site of action when delivered to an animal.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

The following is a description of a specific and illustrative embodiment, wherein the inventors demonstrated that intracellular sigma peptide (ISP) treatment promotes recovery in models of neural injury. Specifically, it was shown that inhibition of CSPG induced signaling of PTPσ, e.g., by ISP treatment, overcomes the CSPG barrier to improve multiple aspects of the functional recovery in a murine stroke model, including general locomotor function, specific upper limb sensorimotor function as well as cognitive function. The mechanism of recovery was also examined. The ISP modulation of PTPσ signaling contributed to several aspects of recovery by inducing migration and sprouting activity in neural cells spared from the injury (i.e., uninjured neurons) that permitted functionality to compensate for the presence of injured neurons. This ultimately permitted induction of ameliorative effects even when ISP treatment was delayed after the neural injury.

First, the efficacy of post-stroke ISP treatment in the C57BL/6 mouse was tested using a proximal middle cerebral artery occlusion (pMCAO) model. Three cohorts of mice (n=59) were subjected to MCAO surgery to induce a large stroke in both striatal and cortical tissue, mimicking a human "malignant" stroke, which tends to be fatal in humans. Stroke mice were subjected to T2 weighted MRI scanning to determine the size of the stroke injury and were grouped blindly into two equally distributed groups that received either daily vehicle (5% DMSO) or daily ISP (20 µg/mouse/day or 30 µg/mouse/day S.C. injections) treatment starting from 24 hours after stroke onset for 6 weeks.

Before the treatment started at 24 hours post-stroke, the mice were characterized by MRI. The data showed that the two groups of animals had no differences in the extent of ischemic injury by MRI scanning (see, e.g., FIGS. 2A and 2B). ISP treatment initiated at 24 hours post stroke (in comparison to the only FDA approved treatment for stroke rtPA's treatment window of 4.5 hrs from stroke onset) was able to improve the survival rate of stroke animals significantly (see, e.g., FIG. 2C). This is possibly due to the effect of an anti-CSPG effect that ultimately counteracts inflammatory and swelling reaction of the brain during the acute phase of stroke.

Figure 3A:
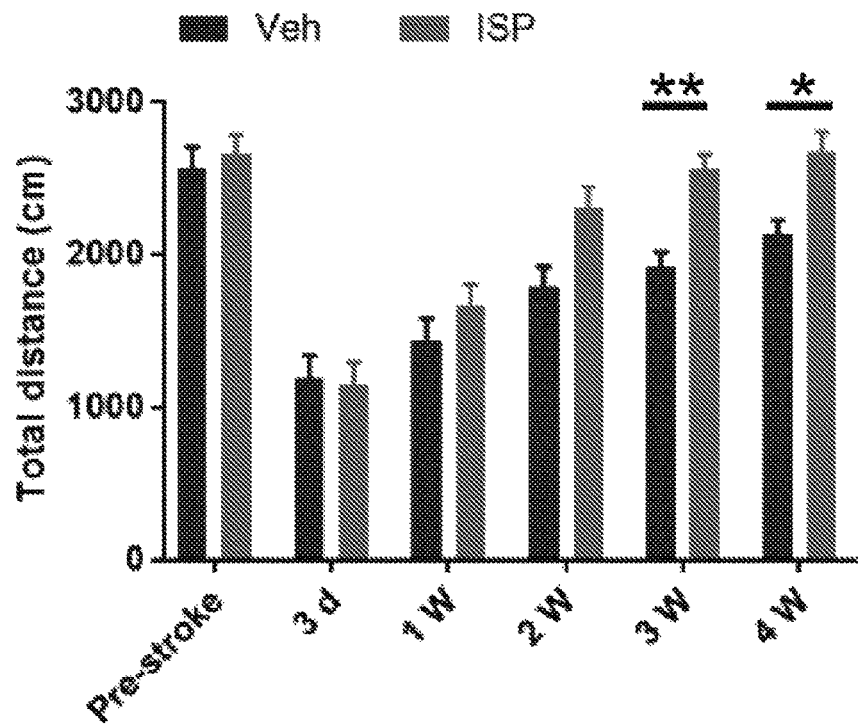
FIGS. 3A-3C graphically illustrate results of computer automated locomotion open field analysis demonstrating enhanced locomotion activity in continuous post-stroke ISP treated mice for parameters of total distance, horizontal activity, and vertical activity, respectively, at 2 weeks to 4 weeks post stroke. n=7-12, *<p<0.05, **, p<0.01, ANOVA.
Figure 3B:
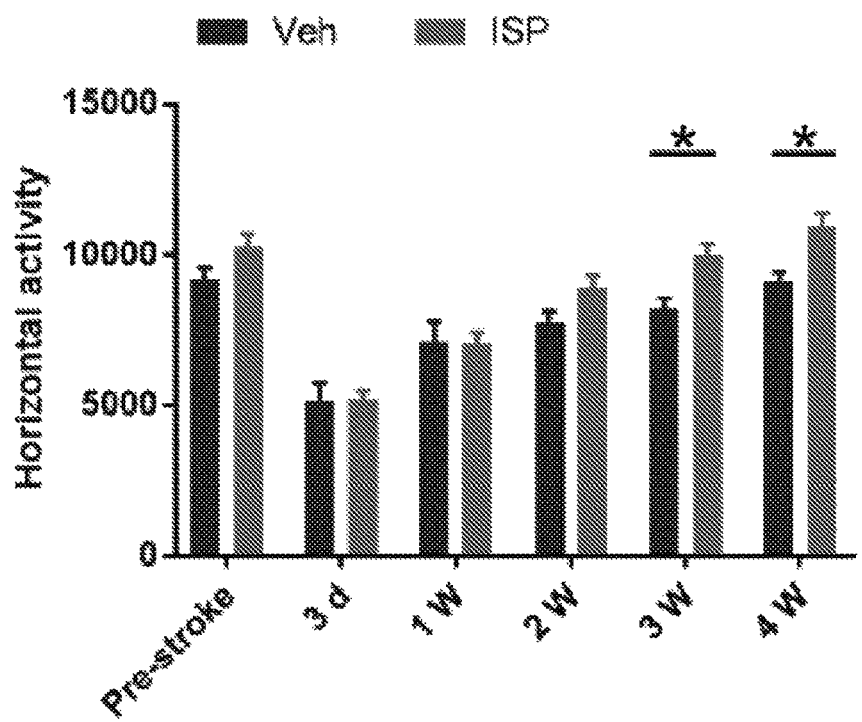
Figure 3C:
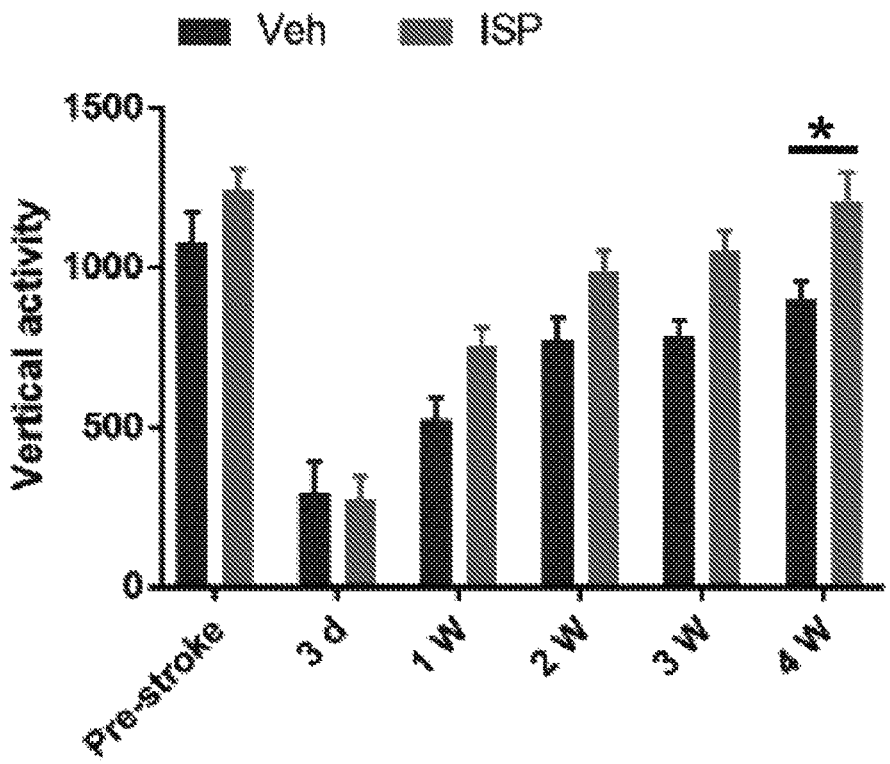

In all the survived mice, using computer monitored automated open field analysis, we found that post-stroke ISP treatment significantly increased the locomotor function in stroke mice at 2-4 weeks after stroke in multiple parameters (i.e., total distance travelled, total horizontal activity, and total vertical activity; see FIGS. 3A, 3B, 3C, respectively).

Figure 4:
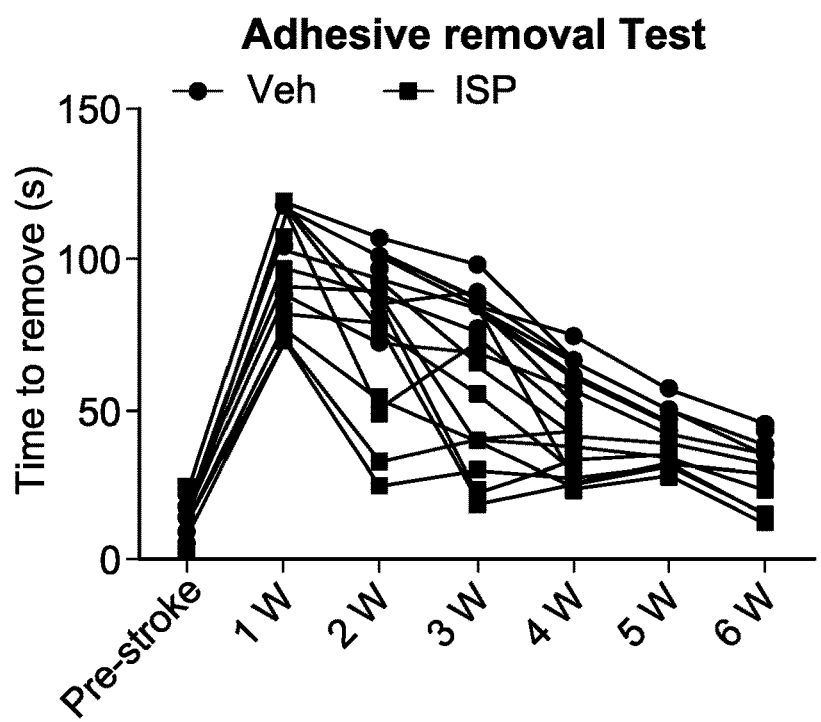
FIG. 4 graphically illustrates post-stroke ISP treatment improves sensorimotor function in stroke affected limbs as measured by adhesive removal test.

Considering that the most common functional deficits following stroke are motor impairments of the contralateral upper limb and more than 90% of human stroke survivors experience sensory deficits, the effect of post-stroke ISP treatment on the performance of stroke mice in a sensorimotor behavioral test (i.e., the adhesive tape removal test) was also examined. In this test, mice need to remove a piece of tape adhered to their affected and non-affected front paws. The data showed that ISP treatment significantly improved the speed that mice were able to remove the tape on the affected limb (without any obvious effects on the unaffected limb). This demonstrates that the result of ISP treatment is specifically related to stroke induced deficits in sensory and motor function (FIG. 4).

Figure 5A:
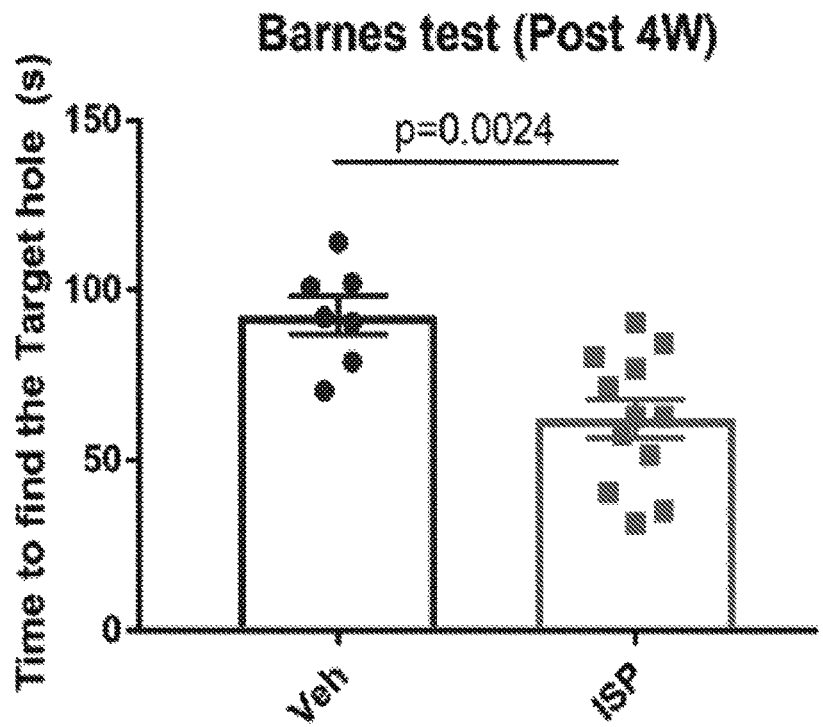
FIGS. 5A-5B graphically illustrate that post-stroke ISP treatment improves cognitive function in stroke mice as measured by time (FIG. 5A) and the number of error trials (FIG. 5B) to find the target hole in Barnes maze.

Cognitive decline is also a major cause of disability in stroke survivors. Accordingly, the effect of ISP treatment on cognitive function in stroke mice was also examined. The Barnes maze test was used to evaluate the learning/memory function in mice. The data showed that ISP treated mice at 4 weeks after stroke used significantly less time as well as less error trials to find the escape hole in the Barnes maze (see FIG. 5A).

Figure 5B:
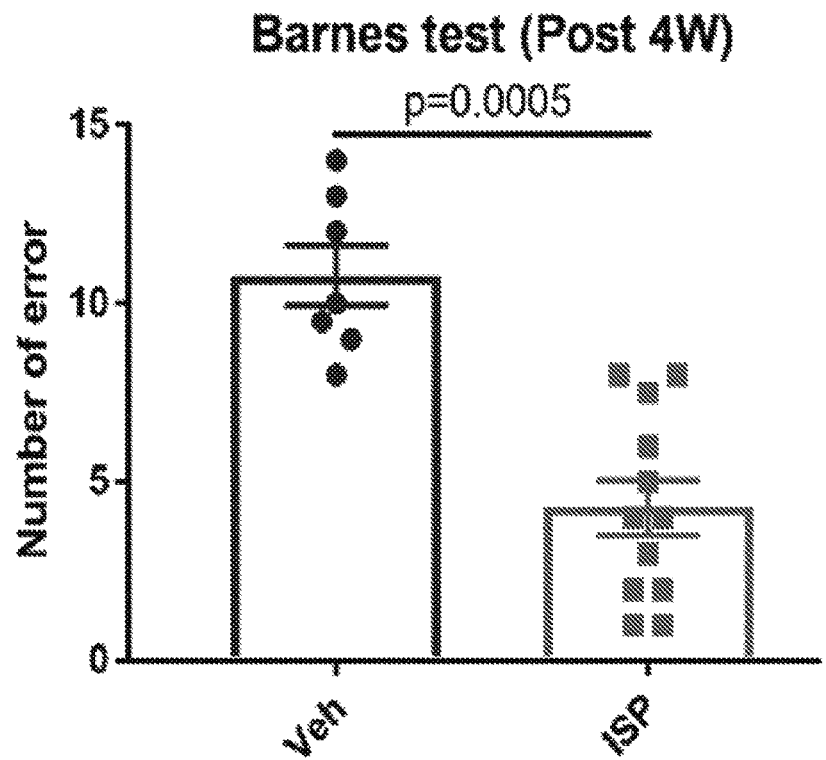

These data demonstrate that systemic ISP treatment improves multiple aspects of the functional recovery in stroke mice, including general locomotor function, specific upper limb sensorimotor function as well as cognitive function. These data also suggest that ISP treatment decreases the chronic atrophy of brain after stroke (see FIG. 5B). The improvement of acute phase survival rate and chronic functions in surviving mice suggest at least two possible mechanisms that can potentially benefit neural injury patients, which therefore offers an attractive and targetable pathway to promote both survival rate after injuries such as malignant stroke and to enhance the long term functional recovery in injury survivors.

Figure 6A:
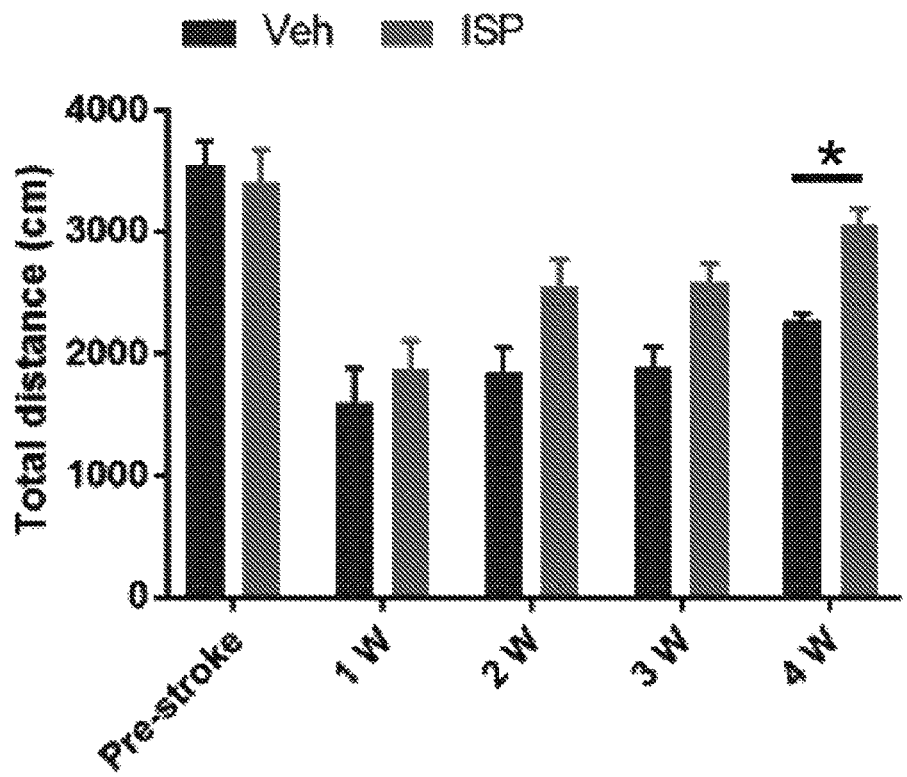
FIGS. 6A-6C graphically illustrate computer automated locomotion open field analysis demonstrating enhanced locomotion activity in delayed (post-stroke day 7) post-stroke ISP treated mice in parameters of total distance (FIG. 6A), horizontal activity (FIG. 6B), and vertical activity (FIG. 6C), respectively, at 4 weeks post stroke. n=7 each group, *,p<0.05 and **, p<0.01, ANOVA.
Figure 6B:
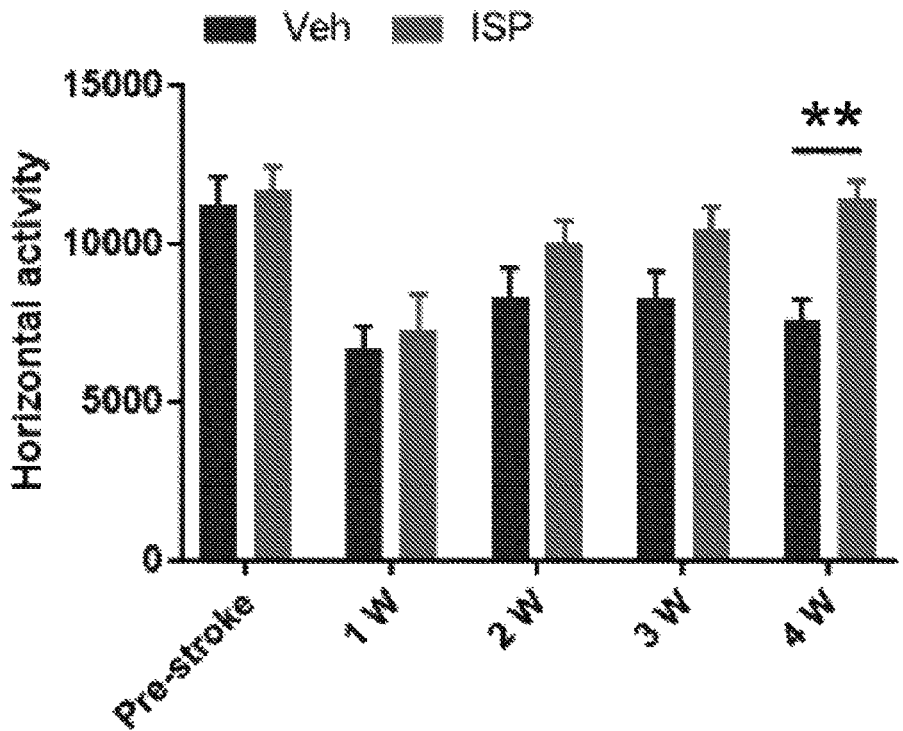
Figure 6C:
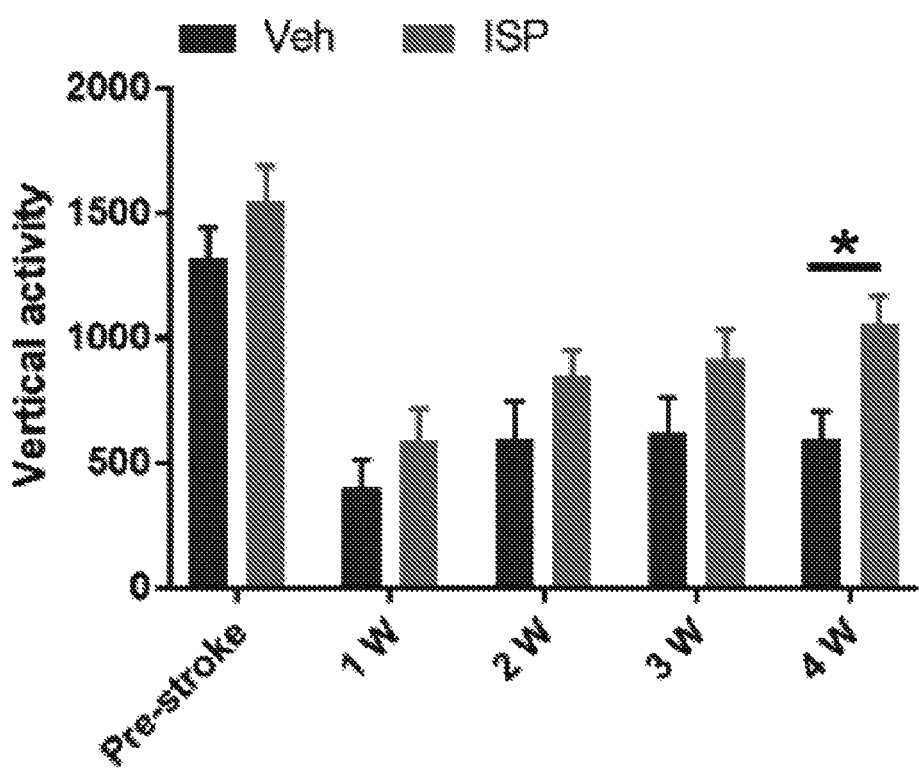
Figure 9A:
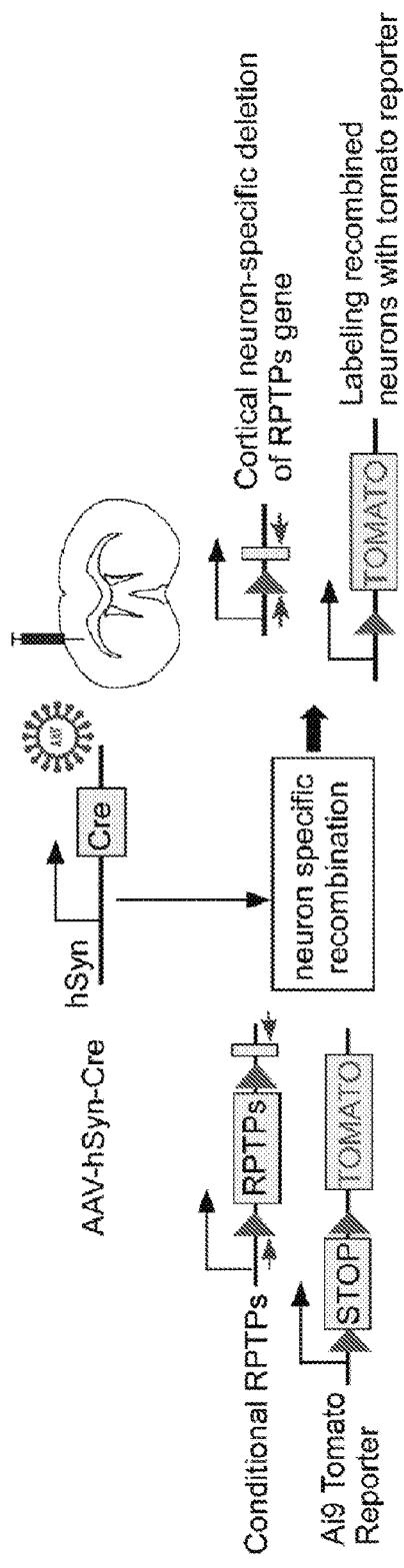
FIGS. 9A-9H illustrate a strategy to assess PTPσ deletion on axonal sprouting mechanisms of neurorepair.
Figure 9C:
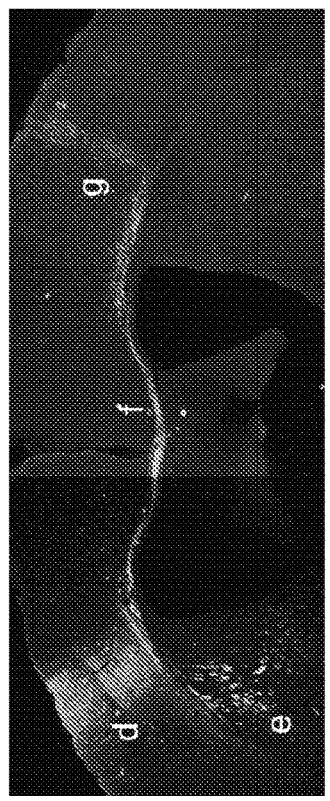
Figure 9B:
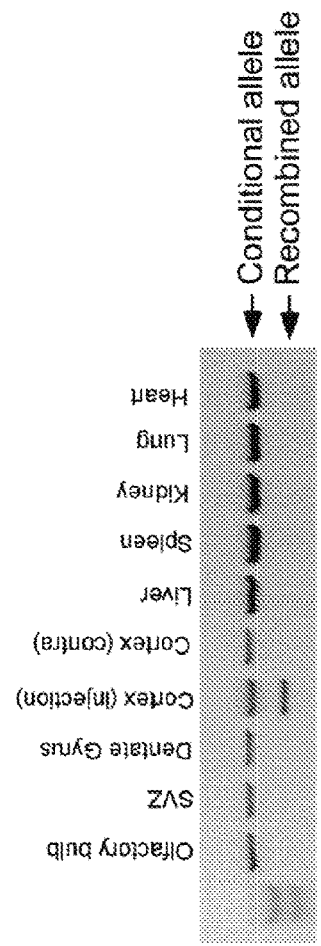
Figure 9D:
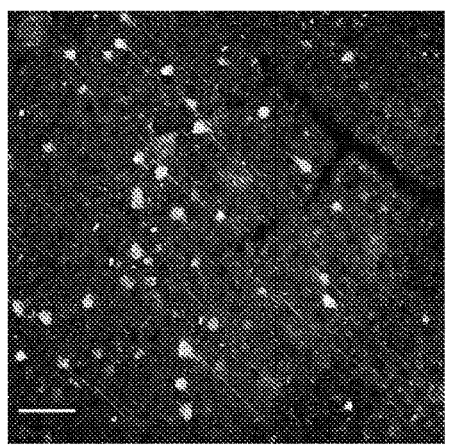
Figure 9E:
Figure 9F:
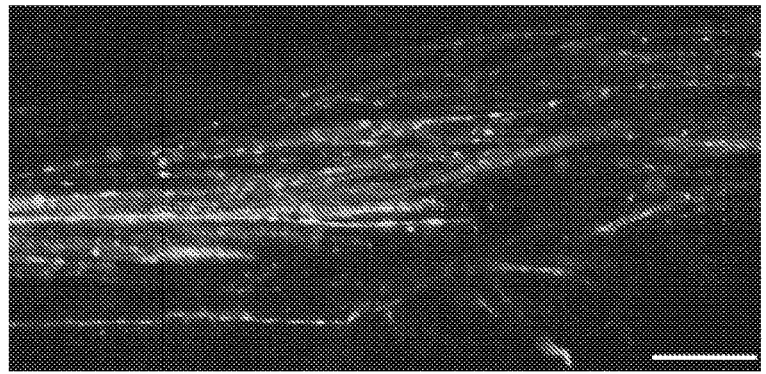
Figure 9G:
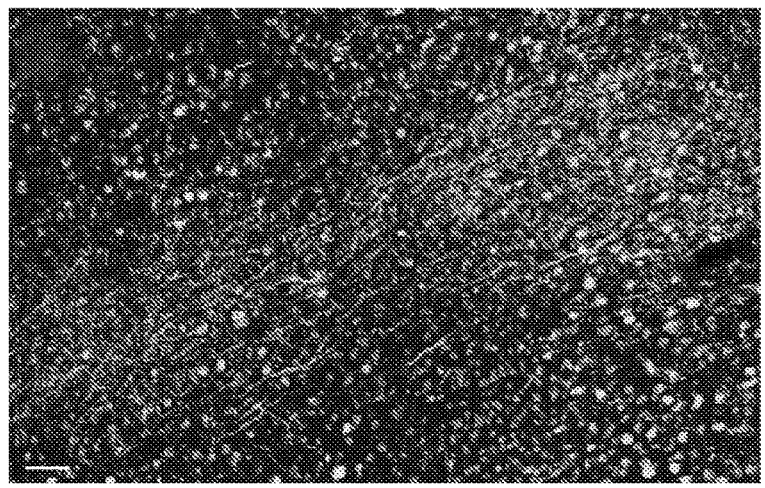
Figure 9H:
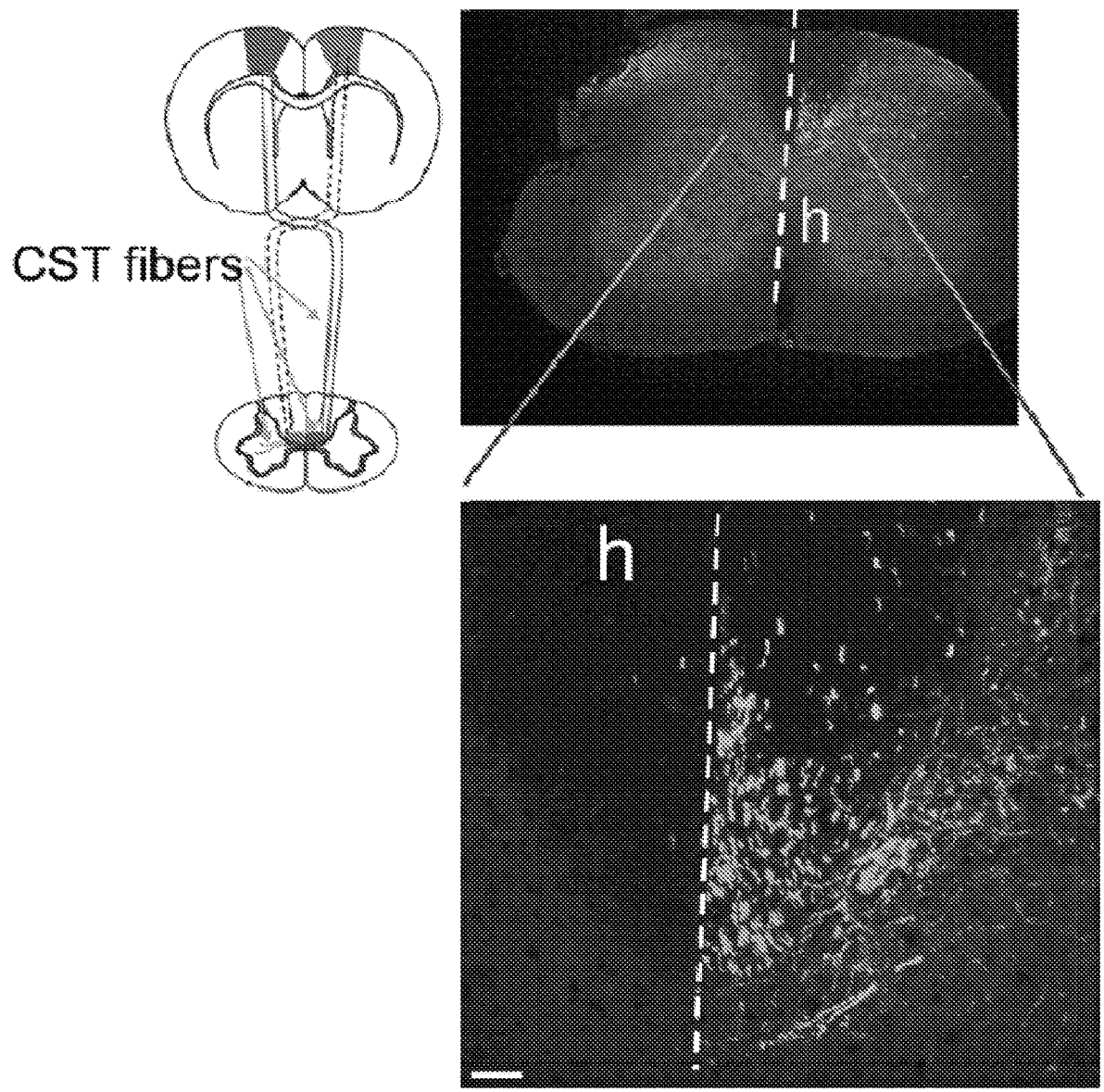

To test the timing of ISP administration relative to the time of injury, and the corresponding effect on recovery, adult C57bl/6J female and male mice were subjected to transient proximal MCAO surgery (35 min) as described above. Animals were subjected to baseline behavioral testing at pre-stroke and 7 days after stroke to ensure no differences exist in the two groups of animals before the initiation of treatment. The efficacy of delayed post-stroke treatment of ISP initiated at 7 days post stroke was tested, a time point when SVZ and SGZ NSCs are activated. Mice receive daily injections of ISP (1 mg/kg/day) or vehicle for 3 consecutive weeks. Open field locomotion tests and adhesive tape removal tests were conducted out every week until 4 weeks after stroke. FIGS. 6A-6C illustrate that the delayed ISP treatment paradigm provided significant effects in improved performance for multiple parameters (i.e., total distance, horizontal activity, and vertical activity, respectively) in the open field locomotion tests by week four. This has significant clinical translational impact because post-stroke seven days as demonstrated here offers a significantly wider treatment window than the current FDA-approved tPA treatment window.

Using the mouse stroke model, ISP treatment was also shown to enhance both neuroblast cell formation and cortical spinal tract axonal sprouting at positions distal to the injury. See FIGS. 7A-7F. As illustrated, these assays demonstrated that post-stroke ISP treatment enhanced DCX+ neuroblasts in post-stroke mice both near the lateral ventricle and adjacent straddle tissues. The post stroke ISP treatment enhanced axonal sprouting from contralateral cortical spinal tract areas. This is the first demonstration of post stroke ISP treatment increasing corticospinal tract projections from contralateral cortex, establishing a mechanism of induced plasticity and spared neural cells.

To further investigate the mechanisms underlying this remarkable functional recovery, described above, from neural injury induced by ISP treatment, an inducible conditional PTPσ knockout model was generated. FIG. 1 schematically illustrates the approach to implement cell specific deletion of PTPσ. PTPσ floxed mice, nestin-CreERT2-PTPσ conditional knockout mice (neural stem cell-specific cKO), and cortical neuronal specific cKO (using AAV-hSyn-cre virus injection in PTPσ floxed mice) were generated. After three generations of crossing, the nestin-CreERT2-PTPσ conditional knockout mice (cKO) were obtained. The cKO mice allow conditional deletion of PTPσ in adult NSCs at desired times. Additionally, AAV-hSyn1-cre injection into the contralateral or para-infarct sites in these conditional KO mice will allow us to specifically the PTPσ gene in mature sprouting neurons at the contralateral or peri-infarct site.

The conditional KO mice were born in the expected Mendelian ratios confirming floxed alleles did not affect the normal development and survival of cKO mice without induction of gene recombination. Cortical neuronal PTPσ mice were generated by injecting AAV-hSyn-cre virus into motor and somatosensory cortex in PTPσ floxed mice. Successful targeting of the floxed allele and recombination of the allele was confirmed in cKO mice in adult NSCs containing brain regions in NSC-specific cKO and in cortical specific recombination in AAV-hSyn-cre injected mice (see FIGS. 1, 8A-8F, and 9A-9H).

FIGS. 8A-8F illustrate that the conditional knockout mice allows the study of the role of the CSPG-PTPσ pathway in neurogenesis and its contribution to functional recovery after neuronal injury, such as stroke. FIGS. 9A-9H demonstrate that the conditional knockout mice permit study of the effect of PTPσ modulation on axonal sprouting mechanisms by injecting AAV-hSyn-cre into the para-infarct area as well as contralateral cortical areas to delete the gene in existing mature neurons at intended times. Peri-infarct injection and contralateral cortical injection in this model allows the distinguishing of the contributions of proximal projection (peri-infarct neurons sprouting) and any distal projection (contralateral cortical neuronal sprouting).

Because initial results show that ISP treatment enhances the number of DCX+ cells migrating towards the infarct zone (see FIGS. 7A-7F, described above), the migration of SVZ NSC's from wild type or cKO PTPσ mice was examined From adult wild type and NSC-cKO mice SVZ, adult neural stem cell (NSCs) neurosphere cultures were established (FIG. 10A). Migration assays demonstrated that nestin (+) NSCs produce CSPGs (FIGS. 10B and 10C). In a CSPG spot assay, it was demonstrated that wild type NSCs cannot cross the rim of the CSPG ring (FIG. 10D), consistent with previous studies. In sharp contrast, cKO NSCs were able to cross the outer rim of the CSPG ring, demonstrating successful abolishment of PTPσ function in cKO NSCs (FIG. 10E).

Figure 12A:
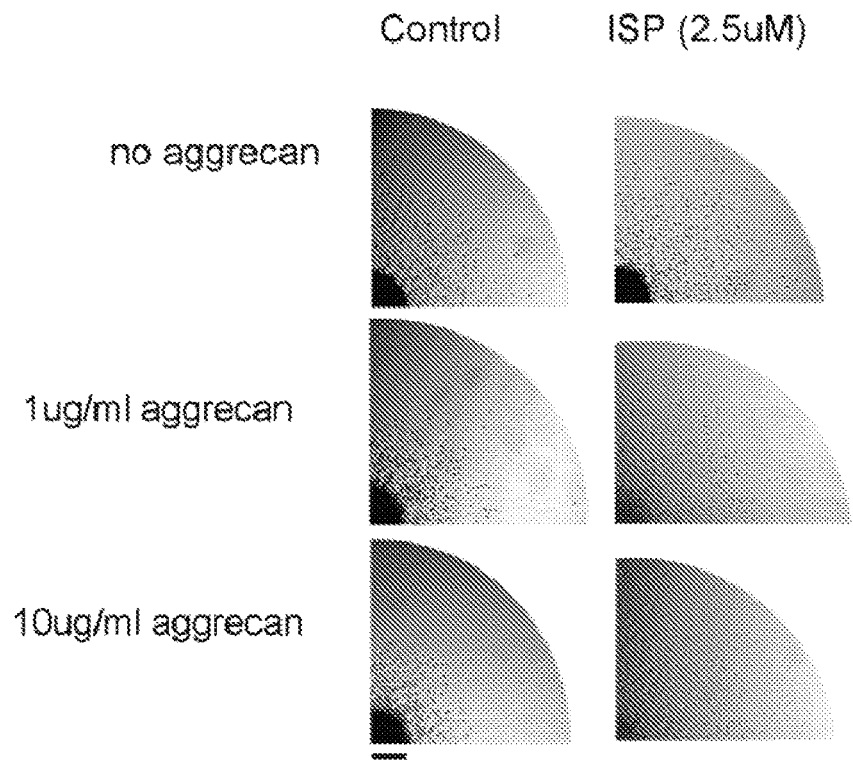
FIGS. 12A and 12B illustrate that pharmacological inhibition of the CSPGs-PTPσ pathway by ISP showed similar results to genetic PTPσ deletion.
Figure 12B:
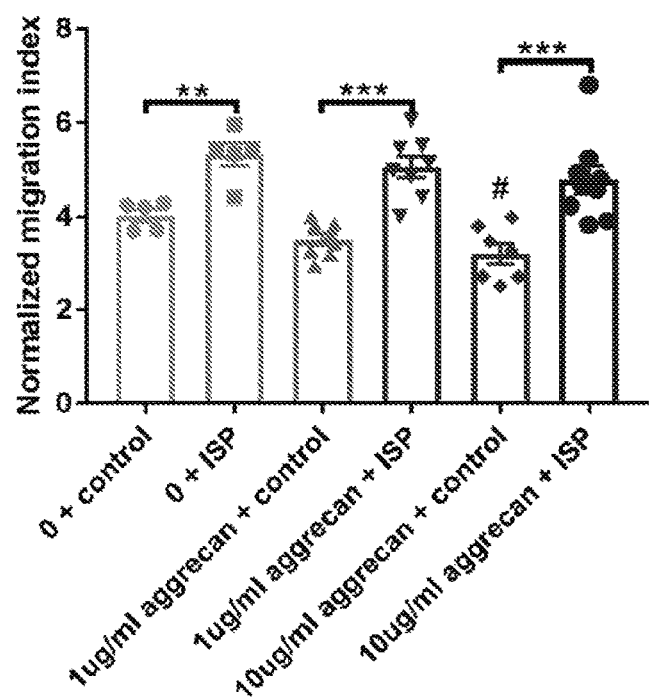
Figure 14A:
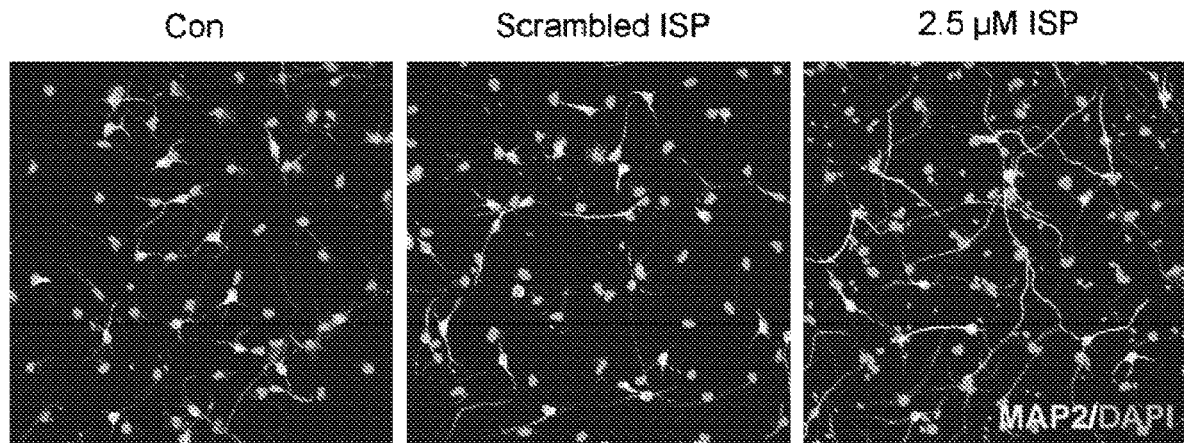
FIGS. 14A and 14B illustrated that ISP treatment enhances neurite outgrowth in WT primary NSCs cells.
Figure 14B:
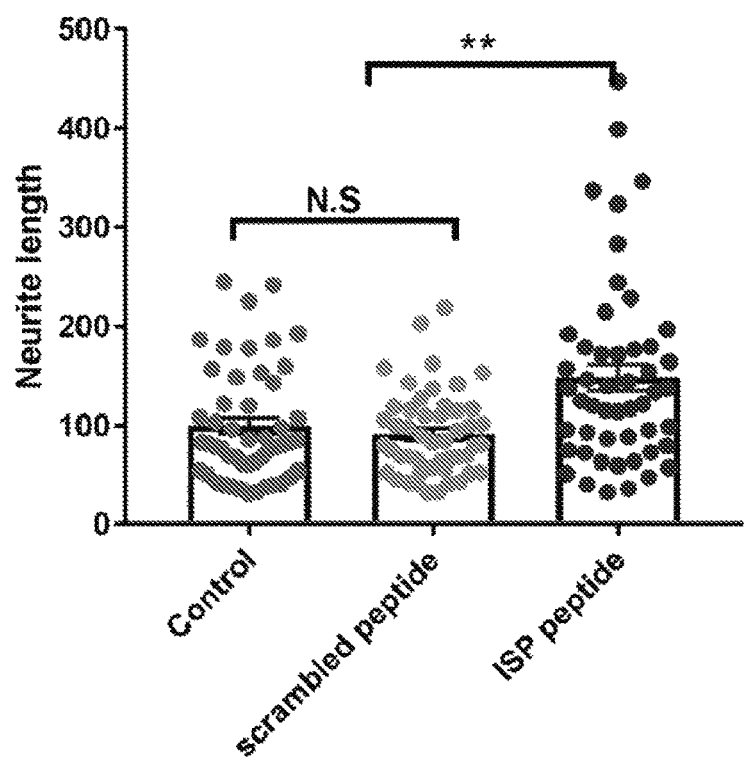

In addition, CSPGs induced PTPσ signaling was demonstrated for the first time to be critical in regulating migration and neurite growth in adult NSCs. Aggrecan substrate coating lead to decreased migration of adult NSCs and deletion of the PTPσ gene in cKO NSC cells results in enhanced migration both under basal levels (no aggrecan coating) and with aggrecan coating (see FIGS. 11A-11E). Pharmacological inhibition of the CSPGs-PTPσ pathway by ISP showed similar results to genetic PTPσ deletion (see FIGS. 12A and 12B). Moreover, both genetic deletion of PTPσ in adult cKO NSCs and pharmacological inhibition of PTPσ by ISP peptide lead to consistently increased neurite outgrowth in differentiated NSCs, while scrambled ISP peptide had no effects (see FIGS. 13A-13C, 14A, and 14B).

In summary, these data obtained from PTPσ conditional knockout mice demonstrated clear functional importance of PTPσ in the basic biology of spared neural cells after neural injury including adult NSCs. The observed functions included neuronal differentiation, neurite outgrowth and migration, which are important cellular mechanisms involved in neurogenesis under basal condition as well as in plasticity after injury, such as stroke. Significantly, it was demonstrated that ISP treatment initiated at even 7 days post-stroke is still effective in enhancing functional recovery. This result is extremely important because there is no therapeutic treatment currently available past the acute treatment window (6 hours pharmacologically and 24 hours surgically) in stroke patients.

The role of the CSPGs-PTPσ pathway has previously been studied more in injured neurons in spinal cord injury (SCI) models because neurogenesis is not a major contributor for neural repair in SCI. However, neurogenesis and migration of DCX+ neuroblasts has now been shown to make functional contributions to recovery after stroke. The present data demonstrates that genetic deletion of PTPσ in adult NSCs and pharmacological inhibition of PTPσ by ISP consistently enhance both neurite outgrowth in newly differentiated neuroblasts and migration of these cells

EXAMPLES

The following examples are provided for the purpose of illustrating, not limiting, the disclosure.

Example

Materials and Methods for the Practice of Various Embodiments of the Disclosure

1. Animals

C57BL/6 mice were purchased from Jackson Laboratory and housed in the animal facility of Case Western Reserve University. Mice were maintained with a 12-hour light/dark cycle and fed ad libitum. All animal protocols were approved by the Institutional Animal Care and Use Committee of Case Western Reserve University. C57BL/6 male mice at 10-12 weeks old of age were used in this study.

2. Murine Model of Transient Focal Ischemia

Transient middle cerebra artery occlusion (tMCAO) was induced in male C57BL/6 mice (12 weeks old, 25-30 g) by intraluminal occlusion of the left MCA for 45 min with silicone rubber-coated monofilament (Cat. 602212PK10Re and 602312PK10Re, Doccol Corporation). Briefly, mice were anesthetized with isoflurance. Body temperature was monitored and maintained at 37±0.5° C. by homeothermic blanket control unit (Harvard apparatus). To minimize animal's pain, mice were subcutaneously injected with buprenorphine. A midline incision was made on skin overlying the calvarium and the skin was pulled laterally to fix a flexible microtip on the surface of the left parietal skull of mice (0.5 mm posterior and 3.5 mm lateral to the bregma). Next, a midline neck incision was made to isolate the left common carotid artery (CCA), external carotid artery (ECA), and internal carotid artery (ICA) of mice. Silicone rubber-coated monofilament was introduced via the arteriotomy in ECA and advanced slowly through ICA toward the orgin of the MCA according to Longa's method. To ensure consistent and successful blockage of MCA, regional cerebral blood flow was monitored in all stroke animals by Laser Doppler flowmetry (PeriFlux system 5000, Perimed, Sweden). After incision closure, mice were subcutaneously given 1 ml warm saline and placed in a heated animal intensive care unit until recovery.

3. Magnetic Resonance Imaging (MRI)

Infarct volumes were measured using a horizontal biospec 9.4 T scanner with a 3-cm birdcage coil (Bruker Inc., Billerica, MA) 23 h after induction of brain ischemia. During MRI scanning procedure, mice were anesthetized with 1.5% isoflurane/oxygen mixture and placed in the cradle in a prone position. The body temperature of mouse was maintained at 33° C. by blowing warm air into the scanner through a feedback control system (SA Instruments, Stony Brook, NY). The respiration rate was also monitored during the experiments. To quantify ischemic edema volume, multi-slice, T2-weighted, axial images were acquired using a rapid acquisition with relaxation enhancement (RARE) sequence with the following parameters: TE/TR, 15/2000 ms; RARE factor, 8; NAV, 4; matrix size, 256×256; slice thickness, 1 mm; number of slices, 13; field of view, 2.4×2.4 cm. Image reconstruction and analysis were performed using in-house developed, MATLAB-based software (Natick, MA, USA). ROIs of ischemic edema volume and brain tissue were drawn from T2-weighted images. Consequently, the percentage of ischemic infarct volume was calculated as following formula: Σ(contralateral area−ipsilateral non-infarct area)/Σcontralateral area×100%.

4. Peptides Preparation

Peptides were purchased from CS-Bio (CA, USA) with >98% purity. Lyophilized peptides were dissolved in sterile water and stored at −80° C. until use. Peptide sequences are as follows:

```
ISP:
                                    (SEQ ID NO: 62)
GRKKRRQRRRCDMAEHMERLKANDSLKLSQEYESI

Scrambled ISP (SISP):
                                    (SEQ ID NO:63)
GRKKRRQRRRCIREDDSLMLYALAQEKKESNMHES
```

5. Systemic Peptide Treatment

Firstly, a vehicle solution of 10% DMSO (1.25 ml DMSO in 23.73 ml sterile saline) was prepared for each mice. Next, appropriate ISP peptide was added to vehicle solution, and then aliquoted into 1.5 ml Eppendorf tubes (each corresponding to a single mouse's daily dose) and frozen at −80° C. The final ISP peptide concentration was 0.3 μg/μl. After MRI scanning, ischemic mice were randomly grouped into two equally distributed groups according the size of the stroke injury. At 24 h post-ischemia and each afternoon thereafter for 6 weeks, mice were subcutaneously injected with ISP (30 μg/day, 100 μl) or vehicle (5% DMSO in saline, 100 μl). Experiments were carried out in a blinded fashion.

6. Quantification of Brain Atrophy in Stroke Animals

The post-stroke 6-week brain sections (25 μm) were mounted on PLL-coated slides. The sections were rehydrated in $KH_2PO_4$ buffer (pH 4.5) for 10 min, and then stained in pre-warm 10% Giemsa solution for 30 min at 42° C. After a brief rinse with $KH_2PO_4$ buffer, sections were dehydrated in absolute ethanol, cleared in xylene and mounted with Histoseal. A set of serial sections was imaged by Path Scan Enabler IV slide scanner. Contralateral and ipsilateral brain areas were quantified using ImageJ software. The calculation formula of atrophy rate is as follows: Σ (contralateral brain area−ipsilateral brain area)/Σ contralateral brain area×100%.

7. Anterograde Tracing and Quantification of Axonal Sprouting

Four weeks after tMCAO, mice were anesthetized with 1.5% isoflurane/oxygen mixture and stabilized in a stereotaxic frame. 1.5 μl of the biotin dextran amine (BDA, MW10,000; 10% in PBS, invitrogen) were injected at three sites in the contralesional cortex (coordinates: 1. A/P 0.0 mm, M/L −2 mm, D/V −1 mm; 2.A/P 0.5 mm, M/L-1.5 mm, D/V-1 mm; 3. A/P 0.5 mm, M/L −2 mm, D/V −1 mm) Two weeks later, brain and cervical spinal cord were harvested after cardiac perfusion with PBS followed by 4% paraformaldehyde. After post-fix overnight in 4% paraformaldehyde and cryoprotection in 20% and 30% sucrose, coronal brain sections and transverse spinal cord sections were cut at 30 μm thickness. For the detection of BDA, sections were rinsed in 0.1M PB and incubated in 0.3% $H_2O_2$ for 30 min to inactivate endogenous peroxidase, followed by incubation for 2 hours with a Vectastain® ABC kit (Vector Laboratories, Burlingame, CA, USA). Staining was developed with 2,3' diaminobenziine tetrahydrochloride (0.5 mg/ml in 0.1M PB). The number and length of midline-cross BDA+ fiber were assessed in a blinded manner Sections were analyzed with ImageJ software.

8. Neurobehavioral Assay

All behavioral tests were performed during the light phase in a blinded fashion. To reduce stresses, mice were acclimated in the behavioral test room 1 h before test beginning. All apparatus were cleaned with 75% ethanol to avoid instinctive odorant between mice.

8.1 Locomotor Function

Mice motor activities were assessed using Accuscan activity monitor (Columbus, OH, USA) one day before and 3, 7, 14, 21, 35 and 42 days after tMCAO as previously described. There are 16 horizontal and 8 vertical infrared sensors (interval 2.5 cm) in this monitor. Each mouse was put into a 42×42×31 cm Plexiglas open box for 1 hour with food and water supply. To avoid observer bias, this locomotor test was automatically monitored by the computer and software. Locomotor activity was calculated by automated Versamax software (Accuscan, Columbus, OH, USA). The following variables were measured: (A) horizontal activity (the total number of beam interruptions that occurred in the horizontal sensors); (B) total distance traveled (cm, the distance traveled by the animals); (C) Vertical activity (the total number of beam interruptions that occurred in vertical sensors).

8.2 Barnes Maze Test

The spatial memory of ischemic mice was examined using Barnes maze (Stoelting Company, WoodDale, IL, USA) 28 days after tMCAO. The maze consists of a 91.5 cm diameter circular platform with 20 holes around the perimeter. Mice were discouraged to idle around aimlessly by blowing fans and a bright light above the platform. At day 0, mice were gently guided to enter the target hole after removing the start chamber. At day 1, mice were trained for 4 trials in 2 sessions to find the escape tunnel placed under the target hole. Once mice entered the target hole, the hole was covered and mice were allowed to stay in it for 2 min. If mice could not locate the target hole within 5 min, mice were guided by the observer to enter the target hole. At day 2, one trial was run and video-taped until the mouse getting into the target hole or stopped at 5 mins when the mouse could not locate the target hole. Time spent to locate the escaping hole and error numbers in finding the hiding hole made by the mouse were measured by an observer in a blinded fashion.

8.3 Adhesive Removal Test

This test was performed on days 7, 14, 21, 28, 35 and 42 post-stroke in order to examine the sensorimotor deficits. Each mice was placed into transparent cylinder (15 cm diameter) during a habituation period of 1 min Thereafter, two different colored adhesive labels (2.5 mm diameter made by punch, Tough Spots) were applied with equal pressure on each mouse's forepaw. The times required to remove the adhesive labels were measured with a maximum of 2 min. To achieve an optimum level of performance, mice should be trained for 4 days before surgery.

9. Neural Stem Cell Culture

Primary stem cells were obtained from C57BL/6J mice at 5 weeks of age. After euthanization, whole brains were immediately harvested and dissected under microscope to obtain the subventricular zone (SVZ) tissue. After mechanical dissociation with a stab knife, the tissue fragment were processed using trypsin and resuspended as individual cells at a density of $10^4$ cell/$cm^2$ in neurobasal media with growth factors (epidermal growth factor and basic fibroblast growth factor) (NBM-GF). Subsequent passaging of cells were performed using Accutase® (innovative #AT-104, CA, USA) every 7 days until the cells established viable lines, and cellular debris was naturally diminished after each passage. At day 4 of each passage, the proliferating spheres were fed with NBM-GF. We used neurospheres at passage P3-P8 in this study.

10. CSPG Gradient Crossing Assay

CSPG gradients were prepared on coverslips as previously described. Briefly, 24-well glass coverslips were coated with poly-L-lysine and nitrocellulose, and a mixture of 700 ug/ml aggrecan (A1960) and 10 ug/ml Laminin (11243217001, Sigma) spotted on the coated coverslip. After drying, coated coverslips were then incubated with laminin at 37° C. for 3 hours. Transfected neural stem cells were plated at a density of $10^4$ cells/coverslip and cultured in NBM-GF medium. After 7 days, the wells were fixed with 4% paraformaldehyde for 15 min at room temperature and stored in phosphate-buffered saline at 4° C. until staining.

11. Migration of Neural Stem Cell on CSPGs

To determine the effects of CSPGs on the migration of neural stem cells in vitro, flat-bottom 48-well plates were first coated with poly-L-lysine overnight, followed by a rinsing with water. Aggrecan (A1960, sigma) were coated onto the 48-well plates at the concentration of 1 ug/ml and 10 ug/ml diluted in sterile water overnight, followed by a rinsing with water. The control wells contained poly-L-lysine alone. Neurospheres of equal size were seeded in each wells in NBM-GF medium with 2.5 μM ISP peptide or scramble peptide (n=7 neurospheres in 7 wells per condition), and the plates were incubated at 37° C. for 21 hours. Thereafter, images of each well were taken using Leica DMi8 widefield microscope. Migration activities were defined as dividing the total area of neurospheres by the inner area of neurospheres. The inner area and total area of neurospheres were measured by ImageJ software. Distance measurements were performed by an observer in a blinded fashion.

12. Neural Stem Cell Differentiation Assay

Briefly, glass coverslips in an untreated 24-well plate were coated with poly-ornithine and laminin After splitting neurospheres during passaging, individual cells were plated at a density of $10^4$ cells/$cm^2$ in 500 μl of NBM-GF. Every other day, 250 μl of media was removed from each well and 300

µl of fresh NBM-GF was added. When the attached cell reached approximately 70% confluency (around day 5), all NBM-GF within each well was gently removed and immediately replaced with neurobasal media without growth factor (NBM) with ISP peptide (2.5 µM) or scramble peptide (2.5 µM). Each well was fed daily by removing 250 µl of the media and adding 300 µl of the media containing ISP or scramble peptide. On Day 5 after complete replacement of the NBM-GF, the wells were fixed with 4% paraformaldehyde for 15 min at room temperature and stored in phosphate-buffered saline at 4° C. until staining.

13 Immunohistochemistry

Mice were anesthetized with avertin and perfused with PBS and 4% paraformaldehyde (PFA). Brain was dissected and post-fixed in 4% PFA overnight at 4° C. and equilibrated in 20% sucrose and 30% sucrose. 25 µm-thick sections were incubated in 4% BSA/0.3% Triton-x100 for 1 hour. After blocking, sections were incubated with primary antibodies overnight at 4° C. and followed by appropriate secondary antibodies conjugated with Alexa fluorescence 488 or 594. The following primary antibodies were used: 5-HT (1:500, Immunostar, Hudson, WI) and CS56 (1:500, C8035, Sigma). For each staining, at least three individual animals/group were examined and images were captured with a fluorescence microscope. Staining was quantified using Image J software (US National Institutes of Health, USA).

14 Immunocytochemistry

Cells cultured on coverslip were fixed in 4% PFA for 15 min, permeabilized in 0.1% Triton-X100 for 10 min and then incubated in 10% normal goat serum for 1 hour. Thereafter, cells were incubated in diluted primary antibodies overnight at 4° C. and followed by appropriate secondary antibody goat anti-mouse or anti-rabbit IgM or IgG conjugated with Alexa Fluor 488 or 594 (1:1000, Invitrogen). The glass coverslips were mounted on a microscope slide in Mowiol containing DAPI (Sigma, St. Louis, USA). The following primary antibodies were used: MAP2 (1:500, AB5622, Millipore), Nestin (1:500, NB100-1604, Novus), and CS56 (1:500, C8035, Sigma). Three coverslips were analyzed per condition. Random selections of field in each coverslip were chosen and imaged by Stereo Investigator Software (MBF Bioscience, Williston, VT, USA), and quantitative data was obtained by using NIH ImageJ software.

15. Statistical Analyses

All studies were analyzed using GraphPad Prism 6.00 software in a blinded fashion. Data are shown as mean±standard error of the mean. Statistically significance was set at $p<0.05$. Statistical analysis was performed by two-tailed unpaired Student's t tests, one-way or one-way ANOVA with posthoc analysis by Tukey's multiple comparison test, Dunnett's multiple comparison test, or Sidak's multiple comparison test. No statistical tests were used to predetermine sample sizes, but our sample sizes are similar to those generally employed in the field.

While illustrative embodiments have been illustrated and described, it will be appreciated that various changes can be made therein without departing from the spirit and scope of the invention.

---

The invention claimed is:

1. A method of promoting compensatory plasticity of spared neural cells of a subject's brain after a neural injury, comprising:
   systemically administering to the subject after the neural injury an effective amount of a therapeutic agent comprising a therapeutic peptide and a transport moiety linked to the therapeutic peptide that facilitates uptake of the therapeutic peptide by a cell, wherein the therapeutic peptide comprises an amino acid sequence with at least 70% identity to SEQ ID NO: 32,
   wherein the neural injury is caused by cerebral focal ischemia, cerebral global ischemia, acute ischemic stroke, malignant stroke, chronic stroke disease, thrombus, or embolism, and the therapeutic peptide induces compensatory neurite outgrowth in the spared neural cells.

2. The method of claim 1, wherein the spared neural cells are neural stem cells.

3. The method of claim 1, wherein the spared neural cells comprise oligodendrocyte progenitor cells (OPCs) and/or glial precursor cells (GPCs).

4. The method of claim 1, wherein the spared neural cells are neurons.

5. The method of claim 1, wherein the neurite outgrowth comprises axonal sprouting of the spared neural cells, dendrite sprouting of the spared neural cells, or dendrite branching of the spared neural cells.

6. The method of claim 1, wherein the peptide induces compensatory migration of spared neural cells toward the neural injury.

7. The method of claim 1, wherein the amino acid sequence has at least 78% identity to SEQ ID NO: 32.

8. The method of claim 1, wherein the therapeutic peptide comprises a substitution of an amino acid of at least one of residue 4, 5, 6, 7, 9, 10, 12, or 13 of SEQ ID NO: 32 for another amino acid, wherein the amino acid residue 4E is substituted with D or Q, amino acid residue 5R is substituted with H, L or K, amino acid residue 6L is substituted with I, V or M, amino acid residue 7K is substituted with R or H, amino acid residue 9N is substituted with E or D, amino acid residue 10D is substituted with E or N, amino acid residue 12L is substituted with I, V or M, and/or amino acid residue 13K is substituted with R or H.

9. The method of claim 1, wherein the therapeutic peptide comprises an amino acid sequence selected from the group consisting of SEQ ID NOs: 1-25 and 32.

10. The method of claim 1, wherein the transport moiety is an HIV Tat transport moiety.

11. The method of claim 1, wherein the transport moiety is linked to the therapeutic peptide by a peptide linker.

12. The method of claim 1, wherein the therapeutic agent comprises an amino acid sequence selected from the group consisting of SEQ ID NOs: 35-61.

13. The method of claim 1, wherein the spared neural cells are contacted with the therapeutic agent within 7 days post injury.

14. A method of treating a neural injury in a subject in need thereof, comprising:
promoting compensatory plasticity in spared neural cells after the neural injury according to claim 1.

15. The method of claim 14, wherein the subject is a human or other non-human mammal.

16. The method of claim 1, wherein the therapeutic agent is systemically administered after an acute treatment window of the neural injury to promote functional recovery and/or inhibit chronic atrophy of the brain of the subject.

17. The method of claim 16, wherein the therapeutic agent is systemically administered to the subject at least 12 hours after the neural injury.

18. The method of claim 1, wherein the stroke comprises chronic stroke disease and the therapeutic agent is systemically administered at an amount effective to promote functional recovery and/or inhibit chronic atrophy of the brain of the subject.

19. The method of claim 10, wherein the therapeutic peptide comprises an amino acid sequence with at least 70% identity to SEQ ID NO: 62.

20. The method of claim 19, wherein the therapeutic peptide comprises an amino acid sequence of SEQ ID NO: 62.

21. A method for inducing compensatory plasticity in a subject comprising:
systemically administering to the subject an effective amount of a therapeutic agent comprising a therapeutic peptide, wherein the therapeutic peptide comprises an amino acid sequence with at least 70% identity to SEQ ID NO: 32,
wherein the subject has suffered a stroke caused by cerebral focal ischemia, cerebral global ischemia, acute ischemic stroke, malignant stroke, chronic stroke disease, thrombus, or embolism; and
wherein the systemic administration is carried out in a manner that the therapeutic peptide induces compensatory neurite outgrowth in spared neural cells.

22. The method of claim 21, wherein the compensatory neurite outgrowth is axonal sprouting in the spared neural cells.

23. The method of claim 21, wherein the compensatory neurite outgrowth is dendrite sprouting in the spared neural cells.

24. The method of claim 21, wherein the systemic administration increases synaptic contact with neighboring, surrounding, or distant neural cells.

25. The method of claim 21, wherein the spared neural cells are oligodendrocyte progenitor cells and/or glial precursor cells.

26. The method of claim 21, wherein the spared neural cells are nestin+ and DCX− neural stem cells or nestin+, apt2− neural stem cells.

27. The method of claim 21, wherein the therapeutic peptide comprises an amino acid sequence of SEQ ID NO: 62.

* * * * *